(12) United States Patent
Johnson

(10) Patent No.: US 11,844,667 B2
(45) Date of Patent: *Dec. 19, 2023

(54) DISARTICULATED COMPRESSION SOCKET

(71) Applicant: Joe Johnson, Windsor, CO (US)

(72) Inventor: Joe Johnson, Windsor, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/930,797

(22) Filed: May 13, 2020

(65) Prior Publication Data
US 2021/0212844 A1 Jul. 15, 2021

Related U.S. Application Data

(63) Continuation-in-part of application No. 16/564,745, filed on Sep. 9, 2019, now abandoned, which is a continuation-in-part of application No. 16/293,355, filed on Mar. 5, 2019, now abandoned, which is a continuation-in-part of application No. 16/014,792,
(Continued)

(51) Int. Cl.
*A61F 2/80* (2006.01)
*A61F 2/76* (2006.01)
*A61F 2/78* (2006.01)
*A61F 2/70* (2006.01)
(Continued)

(52) U.S. Cl.
CPC ............... *A61F 2/80* (2013.01); *A61F 2/70* (2013.01); *A61F 2/76* (2013.01); *A61F 2/78* (2013.01); *A61F 2/7812* (2013.01); *A61F 2/741* (2021.08); *A61F 2/7843* (2013.01); *A61F 2002/5026* (2013.01); *A61F 2002/5027* (2013.01); *A61F 2002/5036* (2013.01);
(Continued)

(58) Field of Classification Search
CPC .... A61F 2/80; A61F 2/7843; A61F 2002/509; A61F 2002/5016; A61F 2002/5026; A61F 2002/5027; A61F 2002/802; A61F 2002/805; A61F 2002/785; A61F 2002/807
See application file for complete search history.

(56) References Cited

U.S. PATENT DOCUMENTS 1,144,681 A  6/1915  Apgar
1,272,179 A  7/1918  Anderson et al.
(Continued)

OTHER PUBLICATIONS

Search Results "adjustable stump socket" Duck Duck Go, Jul. 15, 2016, 5 pages.
(Continued)

*Primary Examiner* — Christie Bahena
(74) *Attorney, Agent, or Firm* — Berg Hill Greenleaf Ruscitti LLP

(57) ABSTRACT

The invention provides for an improved disarticulated compression socket configured to secure a residual limb. The disarticulated compression socket may include a rigid socket frame, and preferably a 3-D printed socket having one or more surface channels that may secure a compression cord optionally positioned within a cord cylinder. Such compression cord may be responsive to a compression actuator and one or more disarticulated compression inserts such that activation of the compression actuator causes the retraction of the compression cord initiating the coordinated inward compression of each of said disarticulated compression inserts securing the residual limb within said socket frame.

18 Claims, 20 Drawing Sheets

Related U.S. Application Data filed on Jun. 21, 2018, now Pat. No. 10,406,003, which is a continuation of application No. 15/341,228, filed on Nov. 2, 2016, now Pat. No. 10,004,614.

(51) Int. Cl.
*A61F 2/50* (2006.01)
*A61F 2/74* (2006.01)

(52) U.S. Cl.
CPC . *A61F 2002/5083* (2013.01); *A61F 2002/762* (2013.01); *A61F 2002/7635* (2013.01)

(56) References Cited

U.S. PATENT DOCUMENTS

| | | | |
|---|---|---|---|
| 1,893,853 A | 1/1933 | Tullis | |
| 3,520,002 A | 7/1970 | Wellington | |
| 4,128,903 A | 12/1978 | Marsh et al. | |
| 4,268,922 A | 5/1981 | Marsh et al. | |
| 4,459,709 A | 7/1984 | Leal et al. | |
| 4,670,998 A | 6/1987 | Pasternak | |
| 4,782,827 A | 11/1988 | Paratte | |
| 4,811,500 A | 3/1989 | Maccano | |
| 4,926,569 A | 5/1990 | Bunch | |
| 5,052,130 A | 10/1991 | Barry et al. | |
| 5,269,078 A | 12/1993 | Cochrane | |
| 5,288,286 A | 2/1994 | Davis et al. | |
| 5,323,549 A | 6/1994 | Segel et al. | |
| 5,405,405 A | 4/1995 | Love | |
| 5,408,761 A | 4/1995 | Gazzano | |
| 5,480,455 A | 1/1996 | Norvell | |
| 5,678,329 A | 10/1997 | Griffin et al. | |
| 5,724,714 A | 3/1998 | Love | |
| 6,077,300 A | 6/2000 | Sabolich et al. | |
| 6,362,387 B1 | 3/2002 | Carlson et al. | |
| 6,393,733 B1 | 5/2002 | London et al. | |
| 6,601,321 B1 | 8/2003 | Kendall | |
| 6,622,401 B2 | 9/2003 | Carroll, III | |
| 6,925,734 B1 | 8/2005 | Schaeffer | |
| 6,991,657 B1 | 1/2006 | Price, Jr. | |
| 7,013,581 B2 | 3/2006 | Greene et al. | |
| 7,089,689 B2 | 8/2006 | Meschan | |
| 7,217,247 B2 | 5/2007 | Dariush et al. | |
| 7,243,444 B2 | 7/2007 | Selner | |
| 7,415,782 B2 | 8/2008 | Carroll, III | |
| 7,441,346 B2 | 10/2008 | Hardy et al. | |
| 7,500,323 B2 | 3/2009 | Rasmussen | |
| 7,509,756 B2 | 3/2009 | Lebo | |
| 7,536,809 B2 | 5/2009 | Meschan | |
| 7,555,847 B2 | 7/2009 | Kendall | |
| 7,596,888 B2 | 10/2009 | Meschan et al. | |
| 7,624,517 B2 | 12/2009 | Smith | |
| 7,650,204 B2 | 1/2010 | Dariush | |
| 7,774,177 B2 | 8/2010 | Dariush | |
| 7,918,811 B2 | 4/2011 | Lussier et al. | |
| 8,079,159 B1 | 12/2011 | Rosa | |
| 8,082,062 B2 | 12/2011 | Dariush | |
| 8,128,587 B2 | 3/2012 | Stevenson et al. | |
| 8,230,618 B2 | 7/2012 | Bruce et al. | |
| 8,323,353 B1 | 12/2012 | Alley et al. | |
| 8,656,918 B1 | 2/2014 | Alley et al. | |
| 8,795,385 B2 | 8/2014 | Bache | |
| 8,858,482 B2 | 10/2014 | Ingimundarson et al. | |
| 8,945,237 B2 | 2/2015 | Cornell | |
| 8,978,224 B2 | 3/2015 | Hurley et al. | |
| 9,044,349 B2 | 6/2015 | Hurley et al. | |
| 9,050,202 B2 | 6/2015 | Bache et al. | |
| 9,248,033 B2 | 2/2016 | Bache | |
| 9,283,093 B2 | 3/2016 | Alley | |
| 2004/0158332 A1 | 8/2004 | Carstens | |
| 2009/0287128 A1 | 11/2009 | Ingimundarson et al. | |
| 2009/0299490 A1* | 12/2009 | Summit | A61F 2/7812 623/53 |
| 2010/0042227 A1* | 2/2010 | Schmidt | A61F 2/80 623/36 |
| 2010/0082116 A1 | 4/2010 | Johnson et al. | |
| 2011/0046528 A1 | 2/2011 | Stevenson et al. | |
| 2011/0071647 A1 | 3/2011 | Mahon | |
| 2013/0123940 A1* | 5/2013 | Hurley | A61F 2/54 623/33 |
| 2014/0163697 A1* | 6/2014 | Sanders | A61F 2/5046 623/36 |

OTHER PUBLICATIONS

Click Medical/Revo Welcome, "Better Together", http://www.clickmedical.co/revo-welcome, Obtained Jul. 20, 2016, 4 pages.
"Orthotics & Prosthetics/Boa Closure System", http://www.boatechnology.com/products/orthotics-prosthetics, obtained Nov. 2, 2016, 2 pages.

* cited by examiner

DISARTICULATED COMPRESSION SOCKET

CROSS REFERENCE TO RELATED APPLICATIONS

This application is a continuation-in-part application, and claims the benefit of and priority to U.S. patent application Ser. No. 16/564,745, filed Sep. 9, 2019, which is a continuation-in-part application, and claims the benefit of and priority to U.S. patent application Ser. No. 16/293,355, filed Mar. 5, 2019, which is a continuation-in-part application, and claims the benefit of and priority to Ser. No. 16/014,792, filed Jun. 21, 2018, now U.S. Pat. No. 10,406,003, issued on Sep. 10, 2019 which is a continuation of, and claims the benefit of and priority to U.S. patent application Ser. No. 15/341,228, filed on Nov. 2, 2016, now U.S. Pat. No. 10,004,614, issued on Jun. 26, 2018, the disclosure of which is incorporated herein by reference.

TECHNICAL FIELD

Generally, the inventive technology disclosed herein relates to the field of prosthetic devices, and more particularly a disarticulated compression socket that may be configured to secure a residual limb.

BACKGROUND OF THE INVENTION

Traditional prosthetic devices typically operate by securing the residual limb into a rigid or semi-rigid socket. A socket may commonly refer to the portion of a prosthesis that fits around and secures a residual limb, and to which prosthetic components, such as a foot, are attached. Traditional prosthetic devices, such as sockets are generally designed to stabilize the skeletal components of the residual limb and allow minimal relative movement between the socket and the residual limb. To effectively support the residual limb and allow for the efficient transfer loads from the residual limb to the ground, the prosthetic sockets are designed to provide a sufficient support to secure the residual limb within the socket, while at the same time allowing sufficient flexibility to allow for circulation and account for other physiological, temporal or environmental changes that may affect the shape and/or volume of the residual.

One significant drawback of traditional prosthetic sockets is the inability to account for shape and volume fluctuations of the residual limb. Traditional prosthetic sockets are generally produced in a fixed or static form such that they do not have the ability to accommodate changes in the residual limb-socket interface. For example, it is known that a number or factors may cause a residual limb to change shape and or present an altered volumetric profile. Shape and volume fluctuations in a residual limb may be due to many factors, including but not limited to: edema, muscle atrophy, weight gain/loss, renal dialysis, salt and water intake, alcohol consumption, menses, changes in wearing time and activity.

Additionally, the act of wearing a prosthetic socket, in combination with the mechanical action of walking, or other movements, causes a reduction in the overall volume of a residual limb over time. When there are shape and volume fluctuations, the residual limb-socket interface is compromised, which can lead to discomfort, pain, destabilizing motion between the socket and residual limb, as well as damage to surrounding soft tissue.

As such, there exists a need for a non-static prosthetic socket that may overcome the limitations of prior traditional systems. The current invention overcomes the limitations of, and indeed surpasses the functionality of traditional static prosthetic socket systems. It is therefore the object of the present invention to provide a simple, versatile, cost effective, non-static prosthetic socket. Specifically, one aim of the present technology is to provide a disarticulated compression socket that may be adjustable, for example through compression or expansion to efficiently secure a residual limb within the body of the socket. Additional aims of the present invention include providing a disarticulated compression socket that ay allow for anatomically directed compression, as well as features to accommodate soft tissue expansion.

Accordingly, the objects of the methods and apparatus described herein address each of the aforementioned problems and goals in a practical manner. Naturally, further objects of the inventive technology will become apparent from the description and drawings below.

SUMMARY OF INVENTION

It is the object of the present invention to provide disarticulated compression socket to address the comprehensive concerns outlined above. Additional objects of the current invention may also provide various disarticulated prosthetics that may modulate their internal volume whether by expansion or compression of specified components to secure the residual limb more efficiently and comfortably within the prosthetic.

As one of several preferred embodiments, the inventive technology may provide for a disarticulated compression socket having a plurality of disarticulated compression insert responsive to one or more compression actuators that may form an efficient large surface area contact with a residual limb when compressed.

An additional aim of the current inventive technology may provide for a disarticulated compression socket having a plurality of disarticulated compression insert responsive to one or more compression actuators that exert a lateral compressive force on a residual limb secured within the prosthetic. This lateral compressive force by the disarticulated compression inserts may conform to the laterally positioned muscle groups of a residual limb allowing for a more efficient compression and securement of the residual limb in the prosthetic. This lateral compressive force may also form an efficient large surface area contact with a residual limb when laterally compressed.

Another aim of the current inventive technology may provide for a disarticulated compression socket having a plurality of disarticulated compression inserts responsive to one or more compression actuators that exert a lateral compressive force with a swivel action on a residual limb secured within the prosthetic. This lateral and swiveled compressive force by the disarticulated compression inserts may conform to the laterally positioned as well as loping muscle groups of a residual limb allowing for a more efficient compression and securement of the residual limb in the prosthetic. This lateral and swiveled compressive force by may also form an efficient large surface area contact with a residual limb when laterally compressed and allowed to swivel to conform to the slope of the residual limb.

Another aim of the current inventive technology may provide for a disarticulated compression socket having one or more lateral release channel that may more efficiently accommodate soft tissue displaced by the compressive force placed on the residual limb. Such lateral release channel may be positioned to conform to major lateral muscle groups to accommodate soft tissue expansion more efficiently, including muscle as well as natural volume expansion of the residual limb.

An additional aim of the current inventive technology may provide for an automatic disarticulated compression socket having a plurality of disarticulated compression insert responsive to one or more compression actuators that automatically exert a compressive force on a residual limb secured within the prosthetic in response to a signal from a sensor, such as a position or pressure sensor. In one embodiment the sensor may continually take and receive position data regarding the position and volume of the residual limb and signal one or more compression actuators to constantly modulate the position of one or more disarticulated compression inserts generating an automatically modulating compressive force on the residual limb. This modulating compressive force, lateral or otherwise, by the disarticulated compression inserts may be pre-set to conform to the anatomical presentation of an individual user's anatomical presentation or may be modulated automatically over time or in response to an external stimulus.

Another aim of the current inventive technology may provide for a disarticulated compression socket having a plurality of disarticulated compression inserts that may be secured by one or more compression bands that may further be secured, and/or adjusted through a band coupler. In one preferred embodiment, one or more compression bands may be interlaced with the socket frame and socket apertures so as to secure one or more disarticulated compression inserts. In this embodiment, the disarticulated compression inserts may be compressed around the residual limb and may more efficiently accommodate soft tissue displaced by the compressive force placed on the residual limb.

In this embodiment, the compression band may generate a lateral compressive force by the disarticulated compression inserts, and independent of the socket frame, which may conform to the laterally positioned muscle groups of a residual limb allowing for a more efficient compression and securement of the residual limb in the prosthetic. This compressive force may also form an efficient large surface area contact with a residual limb when laterally compressed. Moreover, in this preferred embodiment, the compression band may generally replace the need for internally positioned cords responsive to one or more compression actuators. This feature not only decreases the overall weight of the disarticulated compression socket, but significantly reduces the manufacturing cost of the socket.

Another aim of the invention may include a compression band coupler that may secure and adjust the compression generated by a compression band. In this preferred embodiment, one or more compression bands may be easily interlaced with the socket frame and socket apertures so as to secure one or more disarticulated compression inserts against the residual limb. In certain embodiment, the compression band may include elastic and non-elastic bands, straps, as well as wires and cables, and cords among other components.

Another aim of the invention may include a 3-D printed disarticulated compression socket (30). In this embodiment, the rigid socket frame (2) may be produced through a 3-D manufacturing process or device. In one preferred embodiment, the method of making a 3-D printed inner socket (3) may be computer aided. In another embodiment, the inner socket (3) may also be produced through a 3-D manufacturing process or device. In one preferred embodiment, the method of making a 3-D printed inner socket (3) may be computer aided.

Another aim of the invention may include a disarticulated compression socket (1) having a surface channel (31) positioned along the internal surface of the rigid socket frame (2), and preferably the socket frame (2) of an improved 3-D printed disarticulated compression socket (30). In one preferred embodiment, the surface channel may be configured to hold one or more removable cord cylinders (23) having at least one compression cord (35) responsive to at least one cord actuator (7).

Another aim of the invention may include a disarticulated compression socket (1) having a disarticulated compression insert (5) having one or more insert channels (33). In a preferred embodiment, an insert channel (33) may be configured to secure a removable cord cylinder (32) having an internally positioned compression cord (34) responsive to at least one cord actuator (7) such that activation of the cord actuator (7) may cause the compression cord (34) to retract causing the disarticulated compression insert (5) to compress against a residual limb positioned within the internal cavity of the socket frame (2).

Another aim of the invention may include a disarticulated compression socket (1) having a disarticulated compression insert (5) having one or more insert channels (33) that are positioned in an off-set or staggered configuration compared to a surface channel (31) on the internal surface of a rigid socket frame (2). In this preferred embodiment, activation of the cord actuator (7) may cause the compression cord (34) to retract causing the disarticulated compression insert (5) to compress against the residual limb positioned within the internal cavity of the socket frame (2), wherein the staggered configuration may generate a greater transit distance of the disarticulated compression insert (5) generating enhanced compression against a residual limb positioned within the internal cavity of the socket frame (2).

The numerous aims features and functions of the various embodiments of the disarticulated compression socket will become readily apparent and better understood in view of the description and accompanying drawings. The following description is not intended to limit the scope of the disarticulated compression socket system including methods of use and creation as are evidently shown below, but instead merely provides exemplary embodiments for ease of understanding.

BRIEF DESCRIPTION OF THE DRAWINGS

The inventive disarticulated compression socket described with reference to the accompanying drawings which show preferred embodiments according to the device described herein. It will be noted that the device as disclosed in the accompanying drawings is illustrated by way of example only. The various elements and combinations of elements described below and illustrated in the drawings can be arranged and organized differently to result in embodiments which are still within the spirit and scope of the device described herein.

DETAILED DESCRIPTION OF THE INVENTION

The present invention includes a variety of aspects, which may be combined in different ways. The following descriptions are provided to list elements and describe some of the embodiments of the present invention. These elements are listed with initial embodiments; however, it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Figure 1:
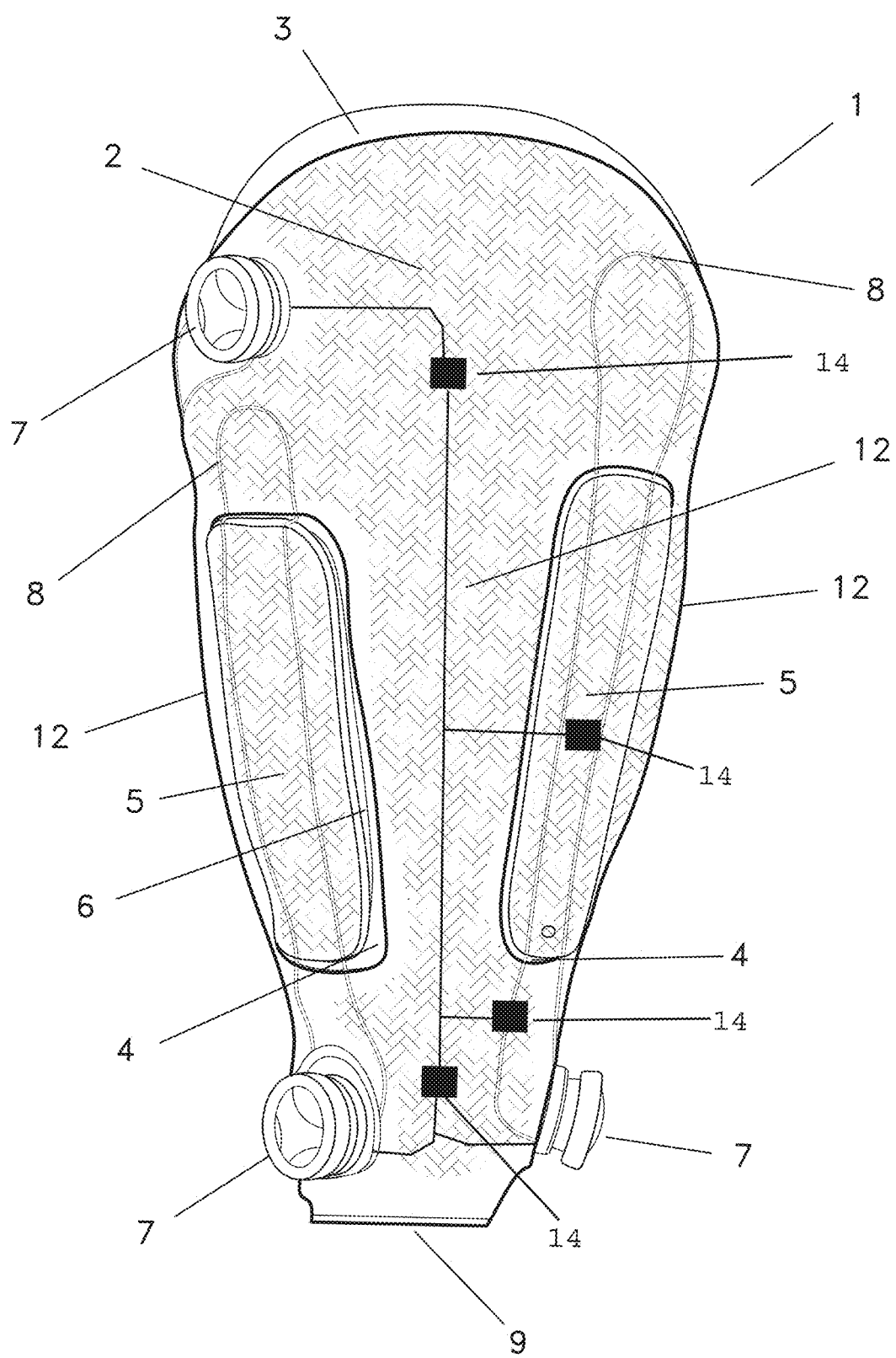
FIG. 1: is a back view of a disarticulated compression socket having a plurality of compression actuators in one embodiment thereof.
Figure 2:
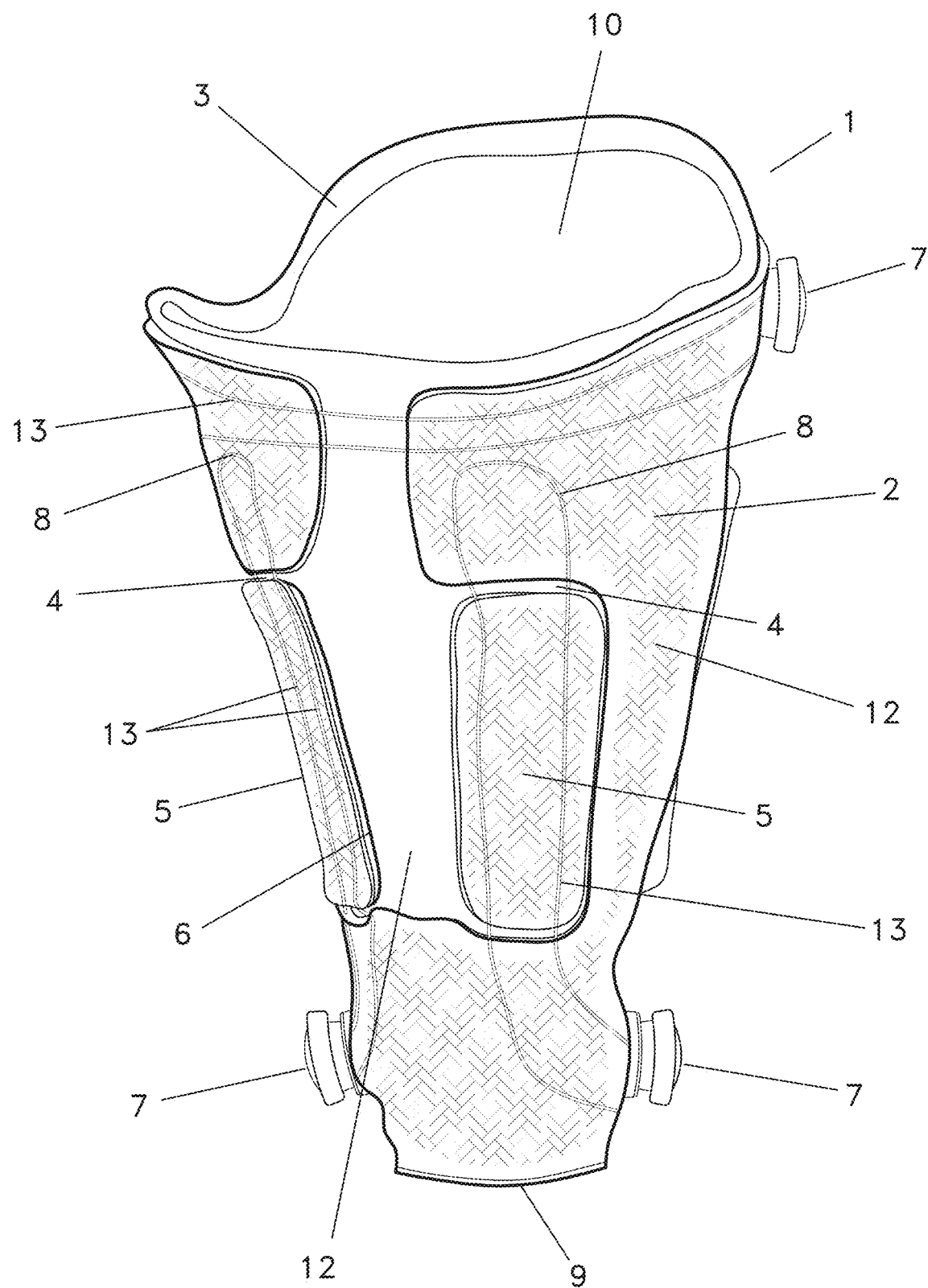
FIG. 2: is a perspective view of a disarticulated compression socket coupled with an inner liner in one embodiment thereof.

Generally referring to FIGS. 1 and 2, in one embodiment the inventive technology may include a disarticulated compression socket (1). In one embodiment, a disarticulated compression socket (1) may include a socket frame (2). As part of the inventive technology, such socket frames (2) may be custom formed to accommodate the anatomical shape of a specific user's residual limb. Considerations of shape, weight distribution, volume and movement may all be considered in forming the socket frames (2) overall shape and configuration. A socket frame (2) may also be coupled with a joint coupler (9) that may be configured to secure additional prosthetic components such as artificial limbs, mechanical devices, as well as shock absorbers and the like.

As shown in FIGS. 1 and 2, a socket frame (2) may be a rigid form configured to accommodate a residual limb (no shown). One exemplary embodiment may include a transfemoral socket frame, or a socket frame (2) configured to accommodate a residual limb wherein the knee joint has been removed and the individual still has part of the femur or thighbone intact. Additional embodiment not specifically shown may also be contemplated, which may include, but not be limited to: a transhumeral socket frame; a transradial socket frame; a transtibial socket frame; a symes socket frame; a hip disarticulation socket frame; a knee disarticulation socket frame; and a wrist disarticulation socket frame and the like.

As noted above, in a preferred embodiment a socket frame (2) may be formed of a rigid material to accommodate and provide a support for a residual limb. In one preferred embodiment, a rigid socket frame (2) may be formed from a variety of material, including but not limited to: plastic, composites, carbon fiber or even an acrylic laminate socket frame with a stiffening component such as carbon fiber and/or para-aremid synthetic fiber.

As shown in FIG. 2, in one embodiment the invention may include a socket frame (2) configured to be capable of securing an inner socket (2) through a socket interface (11). In a preferred embodiment an inner socket (2) may be configured to be secured over a residual limb. In a preferred embodiment this inner socket (3) may be made of a soft, and/or compressible material that may provide a buffer from a rigid socket frame (2). In certain embodiment this inner socket may be made from a variety of materials, such as plastics such as various thermoplastics, rubber, gel, mesh, and silicone as well as various appropriate compressible materials known in the art.

Figure 3:
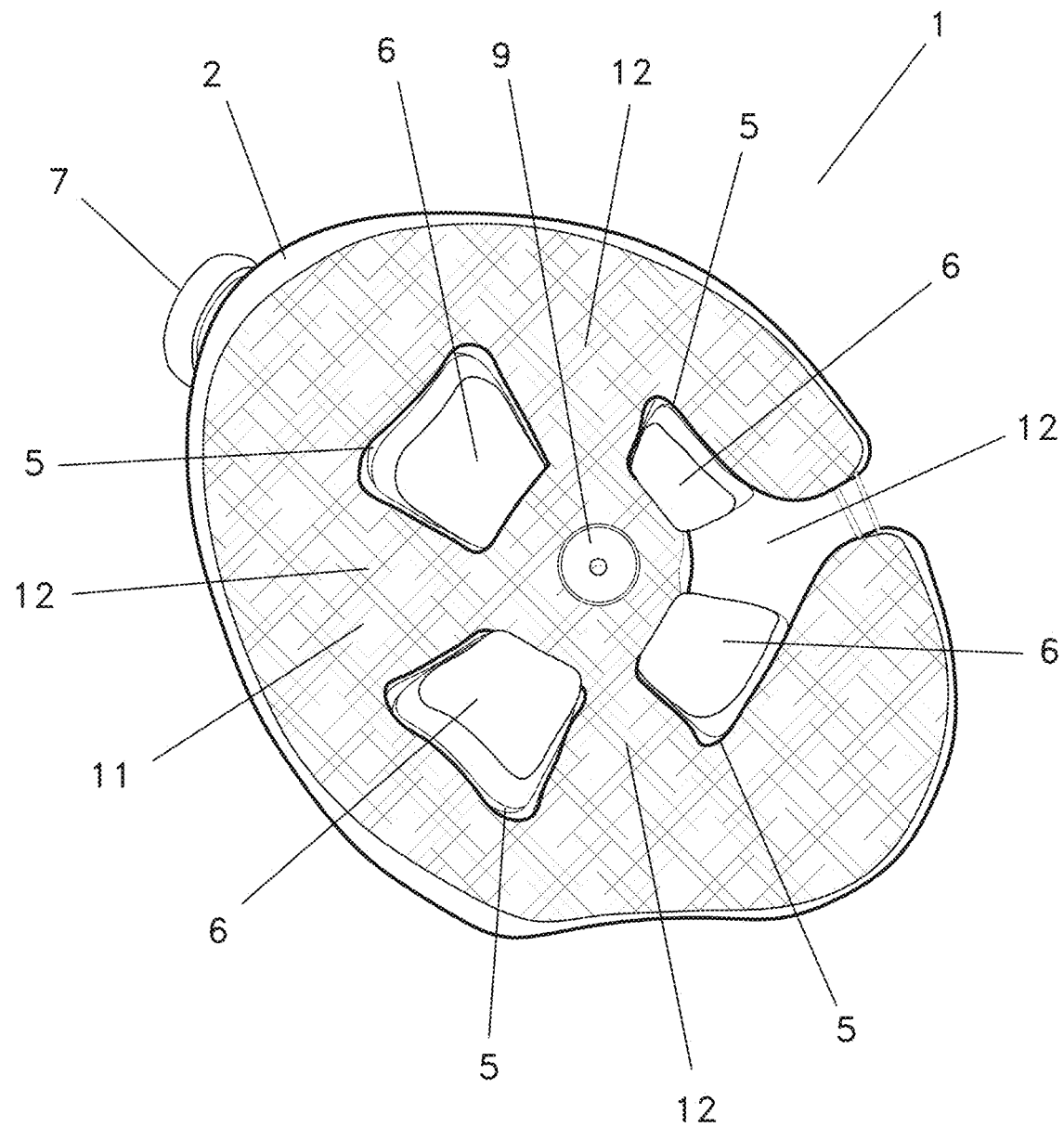
FIG. 3: is a top view of disarticulated compression socket having a plurality of lateral release channels in one embodiment thereof.
Figure 4:
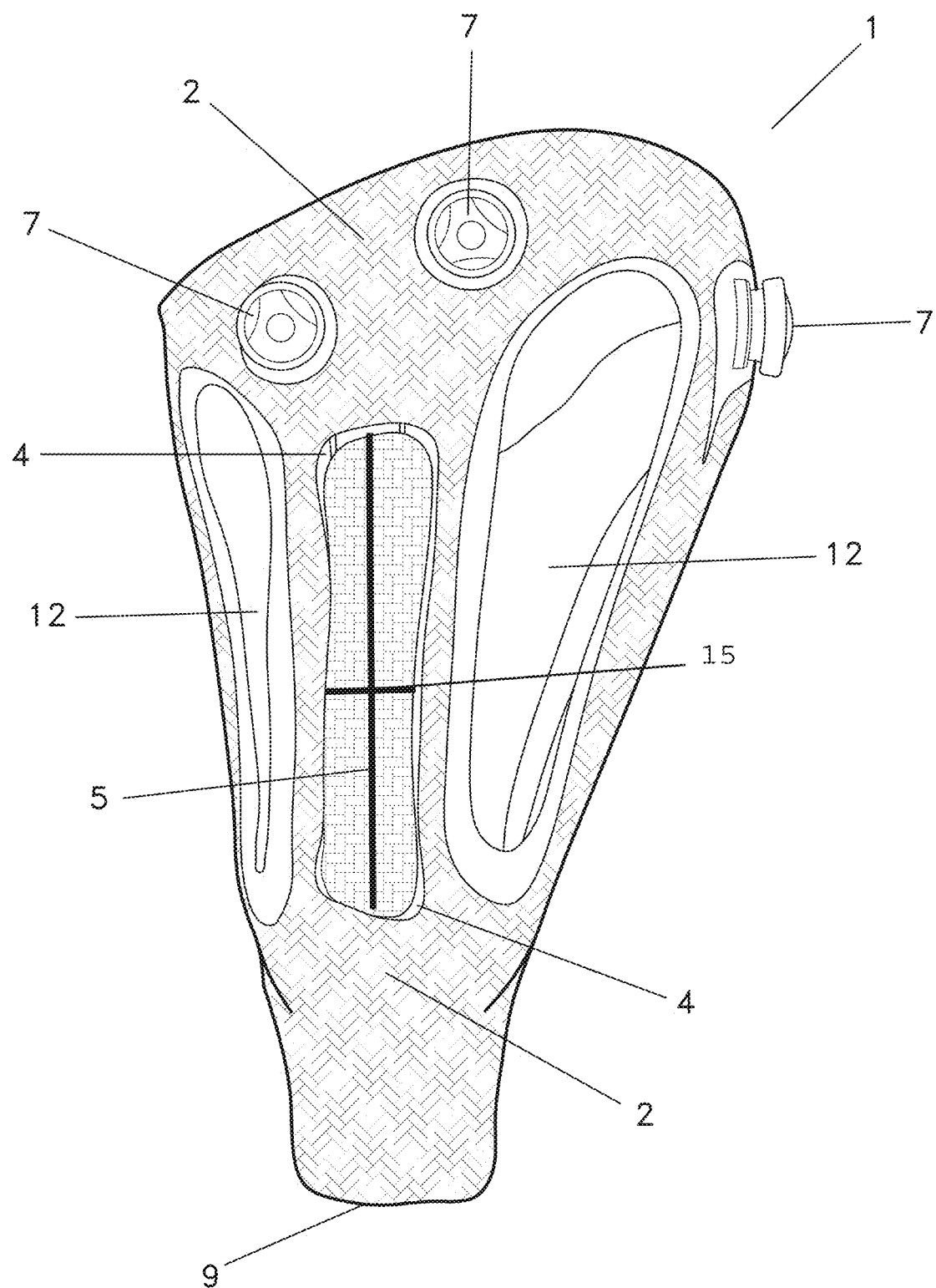
FIG. 4: is a side view of a disarticulated compression socket having a plurality of lateral release apertures in one embodiment thereof.

As shown in FIG. 3, the inner socket include a residual limb interface (10) configured to confirm to the specific anatomical shape of a user's residual limb, and may further have an outer surface configured to secured within the interior of the socket frame (2) or socket interface (11). In one preferred embodiment the residual limb interface (10) may be configured to be closely mated with the user's residual limb providing support and shock adsorption, while the outer surface is configured to be mated with the socket interface (11) on the user's socket frame (2) forming a fitted coupling. While initially described as disparate components, in certain embodiment both the socket frame (2) and inner socket (3) may form an integral component. Additional embodiments not specifically shown may also include coupling devices on the socket frame (2) and/or inner socket (3) configured to secure the residual limb within the inner socket (3), as well as possibly the inner socket (3) within the socket frame (2) itself.

Referring now to FIGS. 1-4, in one embodiment the disarticulated compression socket (1) may include one or more compression apertures (4). As highlighted in FIG. 3, in one preferred embodiment the disarticulated compression socket (1) may include a plurality of compression apertures (4) that may further be configured so as to be in an approximately opposing arrangement. Again, as shown in the preferred embodiment in FIGS. 1-3, the disarticulated compression socket (1) may include compression apertures (4) that include extended apertures positioned laterally, or approximately parallel with the residual limb when it is secured within the socket frame (2).

As shown in FIGS. 1-4, one embodiment the disarticulated compression socket (1) may include one, or even a plurality of disarticulated compression inserts (5). For example, in the preferred embodiment shown in the figures, a disarticulated compression inserts (5) may be positioned within a compression aperture (4). As noted above, while a preferred embodiment may include a disarticulated compression inserts (5), in certain other embodiments such inserts may, in fact be integral with the inner socket (3). In this embodiment, these integral compression inserts may be configured to be sufficiently flexible so as to allow expansion and compression as herein described.

Again, referring to FIGS. 1-4, in one embodiment one or even a plurality of disarticulated compression inserts (5) may be positioned within a compression aperture (4) and further secured in position through a compression actuator (7). In the preferred embodiment shown in FIG. 3, a disarticulated compression insert (5) may include an extended compression surface (6). In this embodiment, an extended compression surface (6) may include a surface that is configured to interface with the residual limb and/or inner socket (3). Again, in this embodiment the extended compression surface (6) may be formed from a compressible material that extends past the surface plane of the socket frame (2) and may form a cushioned interface with the residual limb and/or inner socket (3). Certain embodiments may include but are not limited to: a plastic extended compression surface; a gel extended compression surface; an air filled extended compression surface; a foam extended compression surface; and a composite extended compression surface. Additionally, such extended compression surface (6) may be integral with disarticulated compression insert (5), while other embodiments the disarticulated compression insert (5) may be detachable and/or replaceable. Such detachable and/or replaceable embodiments may include apparatus, such as snap, and/or slide fitted locks to secure the extended compression surfaces (6) disarticulated compression insert (5). Additionally, in such embodiments, the size, shape, and material may be selected and customized so as to conform to the user's specific anatomical presentation as well as mechanical operation needs.

In another embodiment, the invention may include one or more disarticulated compression insert (5) each positioned within a compression aperture (4) and further coupled with a compression actuator (7). In a preferred embodiment, disarticulated compression insert (5) may include an extended compression surface (6) that may be between ¼ and 4 inches in thickness. A compression actuator (7) may be coupled with the disarticulated compression insert (5) having an extended compression surface (6) through one or a plurality of cords (13). In this embodiment, innervation of the compression actuator (7) may cause the retraction of the cords (13) which may in-turn, cause the coupled disarticulated compression inserts (5) having an extended compression surface (6) to contract generating an inward compressive force. This compressive force may work to secure a residual limb within socket frame (2). In this preferred embodiment, one or more cords (13) may be configured to be positioned within a cord channel (not shown) within the socket frame (2). Such a cord channel may include a hollow aperture where a cord may be positioned such that it may be extended and/or retracted. In this embodiment, one or more portions of the cord (13) may be anchored or represent an anchor cord (13)—such components being, in some cases the same. In the preferred embodiment shown in FIGS. 1-2, and 5-6, a cord (13) may be coupled with a compression actuator (7) and further positioned within a cord channel that traverses the socket frame (3) as well as at least one disarticulated compression insert (5).

In still other embodiments, a cord (13) may be coupled with a compression actuator (7) and further positioned within a cord channel that extends horizontally across the disarticulated compression insert (5) having an extended compression surface (6). In this specific embodiment, then the compression actuator (7) is engaged, the cord may be retracted or constricted. Here, because the extended compression surface (6) causes the disarticulated compression insert (5) to extend past the surface of the socket frame (2), the retraction of the cord may allow the disarticulated compression insert (5) to compresses in a manner similar to the lateral compression described herein as the retracting cord is not retracting against the rigid frame of the socket frame (2), but the tractable surface of the extended compression surface (6). In the preferred embodiment shown in the figures, a compression actuator (7) may be coupled with a disarticulated compression insert (5) in such a manner as to secure it within the compression aperture. This compression actuator (7) may further be configured to position and/or secure the disarticulated compression insert (5) such that is freely tractable in one, or multiple directions in response to the action of the actuator. It should be understood that for purposes of this invention a compression actuator may be any apparatus that may be configured to adjust the movement of another portion of a disarticulated compression socket (1). In a preferred embodiment, a compression actuator may be any apparatus that may be configured to adjust the movement of the socket frame (2) and/or a compression actuator may be any apparatus that may be configured to adjust the movement of. Examples of such compression actuators may include a strap compression actuator; an air pressure compression actuator; an automatic compression actuator; a twist compression actuator; and a detachable compression actuator.

Figure 5:
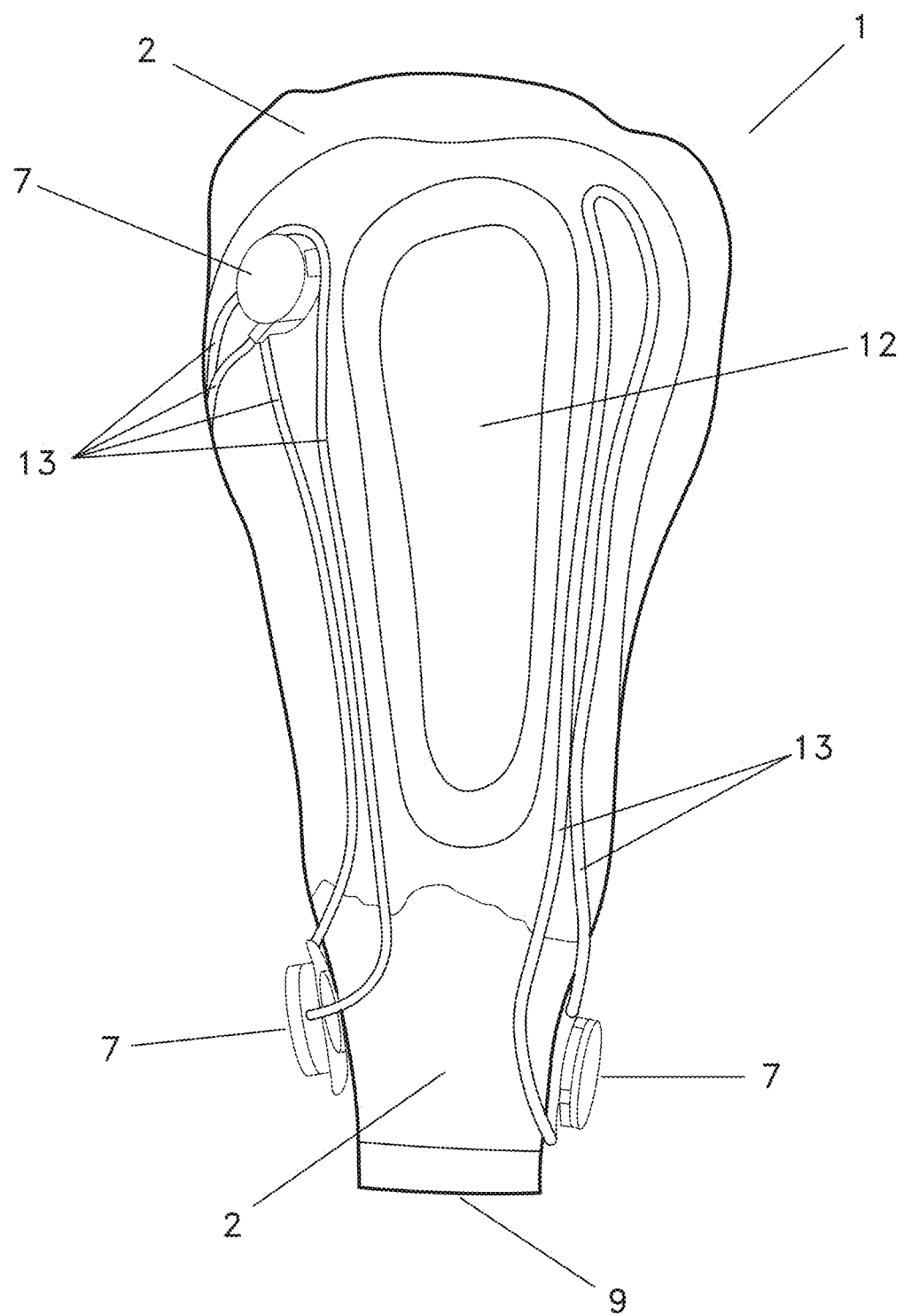
FIG. 5: is an internal view of a disarticulated compression socket having a plurality more internally positioned cords coupled with a compression actuator in one embodiment thereof.
Figure 6:
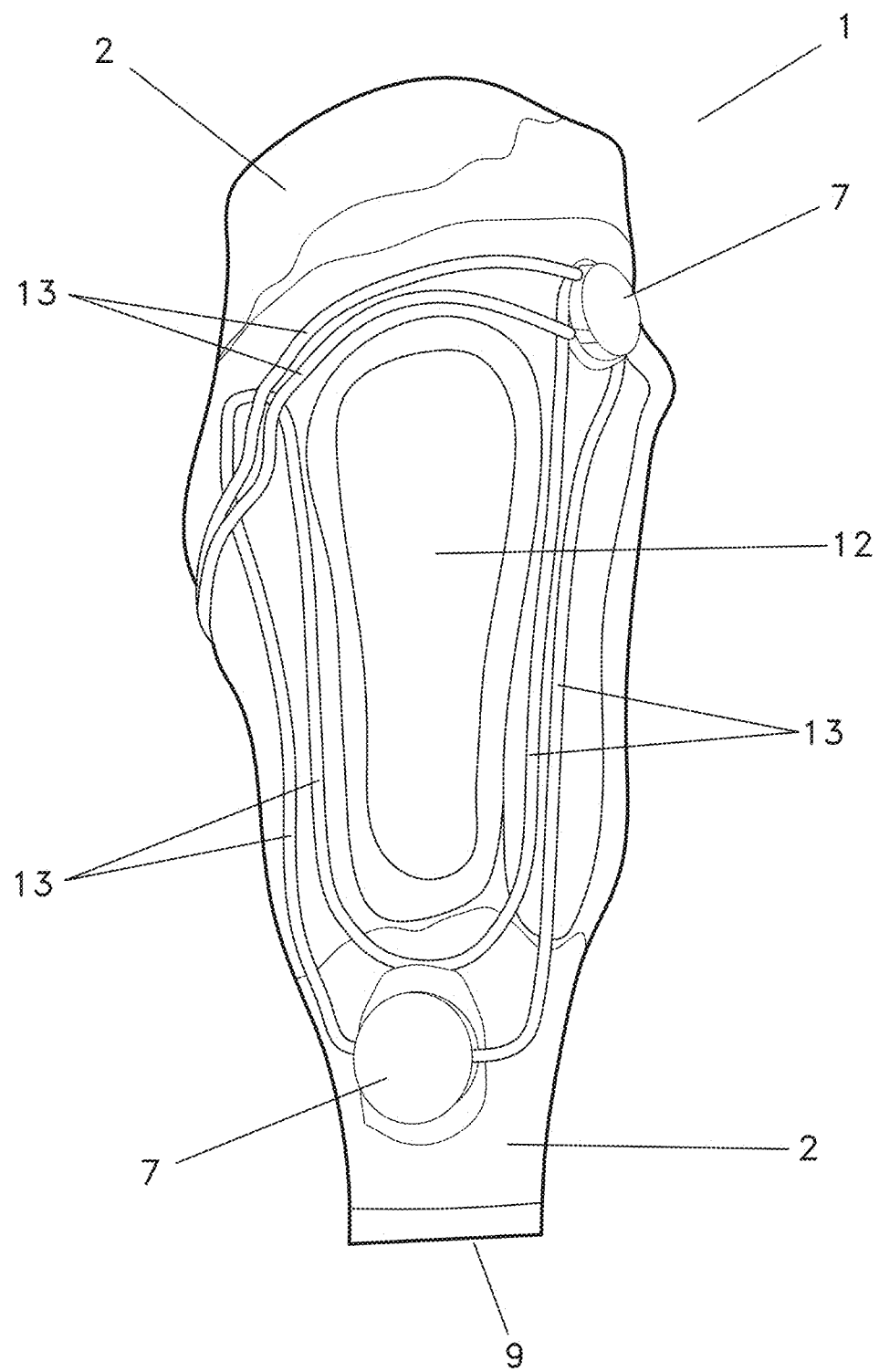
FIG. 6: is an internal view of a disarticulated compression socket having a plurality more internally positioned cords coupled with a compression actuator in one embodiment thereof.

As highlighted in FIGS. 5-6, in this preferred embodiment, a compression actuator (7) may be coupled with the disarticulated compression insert (5) through one or a plurality of cords (13). In this embodiment, innervation of the compression actuator (7) may cause the retraction of the cords (13) which may in-turn, cause the coupled disarticulated compression inserts (5) to proximally contract generating an inward compressive force. This compressive force may work to secure a residual limb within socket frame (2). In this preferred embodiment, one or more cords (13) may be configured to be positioned within a cord channel (not shown) within the socket frame (2). Such a cord channel may include a hollow aperture where a cord may be positioned such that it may be extended and/or retracted. In this embodiment, one or more portions of the cord (13) may be anchored or represent an anchor cord (13)—such components being, in some cases the same. In the preferred embodiment shown in FIGS. 1-2, and 5-6, a cord (13) may be coupled with a compression actuator (7) and further positioned within a cord channel that traverses the socket frame (3) as well as at least one disarticulated compression insert (5). The placement of such cord (13) may couple the disarticulated compression insert (5) to the socket frame (2) while also being responsive to the action of the compression actuator (7).

Again, as shown in the FIG. 2, a portion of the cord, or anchor cord (8) may be secured to a portion of the socket frame (2). In this embodiment one or more cords (13) may be coupled with a compression actuator (7) and further positioned within a cord channel that traverses the socket frame (3) as well as at least one disarticulated compression insert (5) and then be secured in a position above the disarticulated compression insert (5). In this embodiment, innervation of the compression actuator (7) may cause retraction of the cord (13), which in this embodiment has sufficiently elastic properties to allow it to be stretched in response to the compression actuator (7). The anchor cord (8) being secured, in this embodiment by the socket frame (2) may not retract, this acting as an opposing force to the compression actuator (7) which may effectuate the cords (13) stretching and in turn, the movement of the disarticulated compression insert (5).

Referring specifically to FIGS. 1 and 2, in one preferred embodiment a compression actuator (7) may be laterally coupled with the disarticulated compression insert (5) through one or more laterally positioned cords (13). In this embodiment, innervation of the compression actuator (7) may cause the retraction of the cords (13) which may in-turn, cause the coupled disarticulated compression inserts (5) to proximally contract generating an inward lateral compressive force, where lateral in this instance may mean approximately parallel with the residual limb thereby generating a large surface area connection when it is secured within the socket frame (2). Lateral may also include the swivel action of the distal ends of a disarticulated compression insert (5). Such swivel action may allow the disarticulated compression insert (5) to conform to the surface of a sloping residual limb thereby generating a large surface area connection.

In another embodiment, a compression actuator (7) may be coupled with the disarticulated compression insert (5) through one or a plurality of straps (not shown). In this embodiment, innervation of the compression actuator (7) may cause the retraction of the straps which may in-turn, cause the coupled disarticulated compression inserts (5) to proximally contract generating an inward compressive force. This compressive force may work to secure a residual limb within socket frame (2).

In another embodiment, a twist compression actuator (7) may be coupled with the disarticulated compression insert (5) through one or a plurality of cords (13) and/or straps (not shown). In this embodiment, twisting of the twist compression actuator (7) may cause the winding-up of the cord(s) (13 and/or straps or other components causing the coupled disarticulated compression inserts (5) to proximally contract generating an inward compressive force. This compressive force may work to secure a residual limb within socket frame (2).

In another embodiment, an air pressure compression actuator (7) may be coupled with the disarticulated compression insert (5) through one or a plurality of pressurized and/or hydraulic absorbers. In this embodiment, innervation of the compression actuator (7) may cause the expansion of the pressurized and/or hydraulic absorbers which may cause the coupled disarticulated compression inserts (5) to proximally contract generating an inward compressive force. This compressive force may work to secure a residual limb within socket frame (2).

Additional embodiments include a compression actuator (7) that may be detached from the disarticulated compression socket (1) and perhaps separately stored when not in use. In additional embodiments, a compression actuator (7) may be coupled, for example through one or more cords (13); a plurality of disarticulated compression inserts (5). In one such embodiment, a compression actuator (7) may be coupled with a plurality of disarticulated compression insert (5) through one or more cords (13). In this embodiment, innervation of the compression actuator (7) may cause the retraction of the cords (13) which may in-turn, cause the coupled disarticulated compression inserts (5) to proximally contract in unison generating an inward compressive force. This compressive force may work to secure a residual limb within socket frame (2). In certain embodiments, multiple compression actuators (7) may be employed allowing varying levels of inward compressive force to be generated from the action of the disarticulated compression inserts (5). Such embodiments may be particularly useful in forming a customized fitted interface between the socket frame (2) and the residual limb and/or inner socket (3) that may conform to the user's specific anatomical presentation as well as mechanical operation needs. Naturally, any such compression actuator (7) may also be de-innervated, or release alleviating the inward compressive force of any coupled disarticulated compression insert (5). In this manner, a user may select the optimal compressive force he or she wishes to apply to the residual limb by each of the disarticulated compression inserts (5) through modulation of the various compression actuators (7).

As shown in FIGS. 1-4, in one embodiment of the inventive technology may include lateral release channel (12) to accommodate the expansion of soft tissue as compressive force is applied to the residual limb. In one preferred embodiment, a socket frame (2) may be configured to include plurality of lateral release channels (12) configured to accommodate soft tissue expansion of the residual limb when disarticulated compression inserts (5) may be compressed to secure said residual limb within said socket frame. In certain preferred embodiments, such lateral release channels (12) may include expanded channels that extend laterally along the socket frame (2), while in other embodiments, such lateral release channels (12) may include apertures in the socket frame (2), such as those described in FIG. 4. These apertures may also extend laterally along the socket frame (2). In some embodiments such lateral release channels may be customized to conform to the anatomical presentation of the residual limb, including major muscle groupings as well as considerations of high and low pressure points along the residual limb interface (10) and/or socket interface (11). Additional embodiments may also include an inner socket (3) having one or more lateral release channels (12). Such lateral release channels (12) may correspond to lateral release channels (12) on the socket frame (2) or may be positioned independently based on the anatomical presentation of the residual limb, including major muscle groupings as well as considerations of high, and low pressure points along the residual limb interface (10) and/or socket interface (11).

As shown in FIG. 1, one embodiment of the invention may include an automatically adjusting compression prosthetic. In this preferred embodiment, one or more sensors (14), such as a position and/or pressure sensor, may be positioned on the prosthetic and further configured to sense the position of the residual limb. In the embodiment shown in FIG. 1, a sensor (14) may be secured to the socket frame (2). In some embodiments a sensor (14) may be integrally connected to the socket frame (2) or may be attachable and detachable. Additional embodiments may include a sensor that may be coupled with one or more disarticulated compression insert (5), cords (13) or even compression actuators (7).

In one preferred embodiment such sensor (14) may be configured to detect the position of the residual limb within the socket frame (2) and send a signal, such as a wired or wireless signal, to a compression actuator (7) causing its innervation. As a result of this innervation, a compression actuator (7) may adjust the position of any coupled disarticulated compression inserts (5) in response to a signal from said sensor. For example, in response to a signal that the residual limb interface (10) and socket interface (11) are in a sub-optimal position, the sensor may send a signal to a compression actuator (7) causing it to modulate the position of any coupled disarticulated compression inserts (5) through release and expansion, or increasing compression on the residual limb.

In certain embodiments a plurality of sensor may be used to innervate a plurality of individual compression actuators (7). In this preferred embodiment, a plurality of disarticulated compression inserts (5) may each be independently modulated in response to an external stimulus, such as position or volume of the residual limb within a socket frame (2) and the like. Additional embodiments may include one or more pre-set sensors (14) and/or compression actuators (7). In this preferred embodiment, one or more compression actuators (7) may be pre-set to adjust the compressive force of the disarticulated compression insert (5), for example in response to a signal from a sensor (14). Individual users may pre-set one or more compression actuators (7) to automatically confirm to the user's specific anatomical presentation as well as mechanical operation needs. Such pre-settings may be further configured to modulate in response to environmental stimuli, such as position or volume of the residual limb within a socket frame (2), or on a timer-base system.

As noted above, in certain embodiments, the inventive technology may accommodate and secure a residual limb within a disarticulated compression socket (1). In a preferred embodiment compression, lateral or otherwise may result in the reduction of the volume of the residual interface (10) as shown in FIG. 3. As part of the invention, compression, including lateral compression of the coupled disarticulated compression inserts (5) may include, but not me limited to: compression of the coupled disarticulated compression inserts (5) resulting in at least a 5% reduction in the volume of the residual limb interface (10); compression of the coupled disarticulated compression inserts (5) resulting in at least a 10% reduction in the volume of the residual limb interface (10); compression of the coupled disarticulated compression inserts (5) resulting in at least a 15% reduction in the volume of the residual limb interface (10); compression of the coupled disarticulated compression inserts (5) resulting in at least a 20% reduction in the volume of the residual limb interface (10); compression of the coupled disarticulated compression inserts (5) resulting in at least a 25% reduction in the volume of the residual limb interface (10); and compression of the coupled disarticulated compression inserts (5) resulting in at least a 30% reduction in the volume of the residual limb interface (10).

Figure 7:
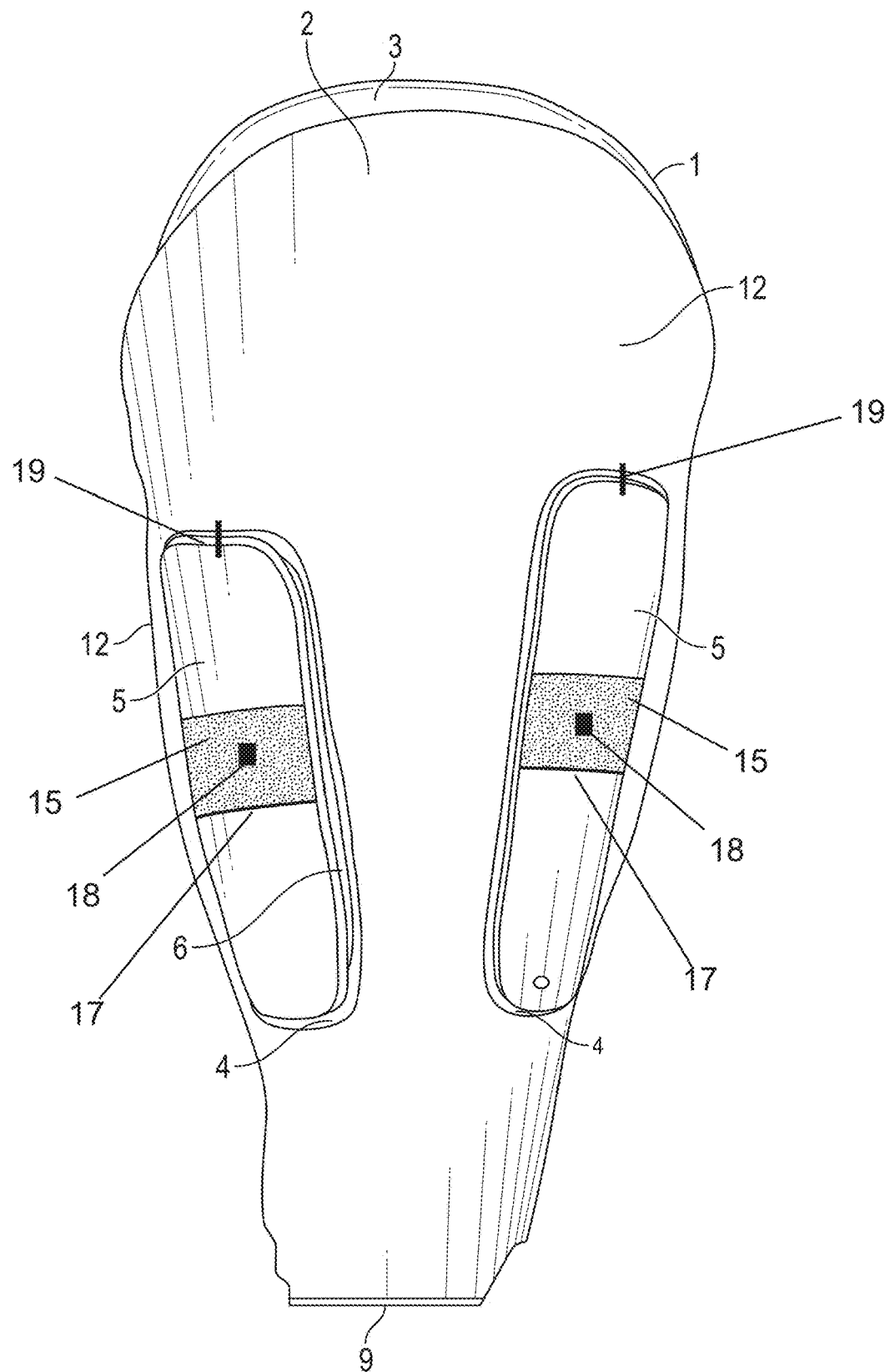
FIG. 7: is a back view of an interlaced disarticulated compression socket having a compression band securing a plurality of compression inserts in one embodiment thereof.
Figure 8:
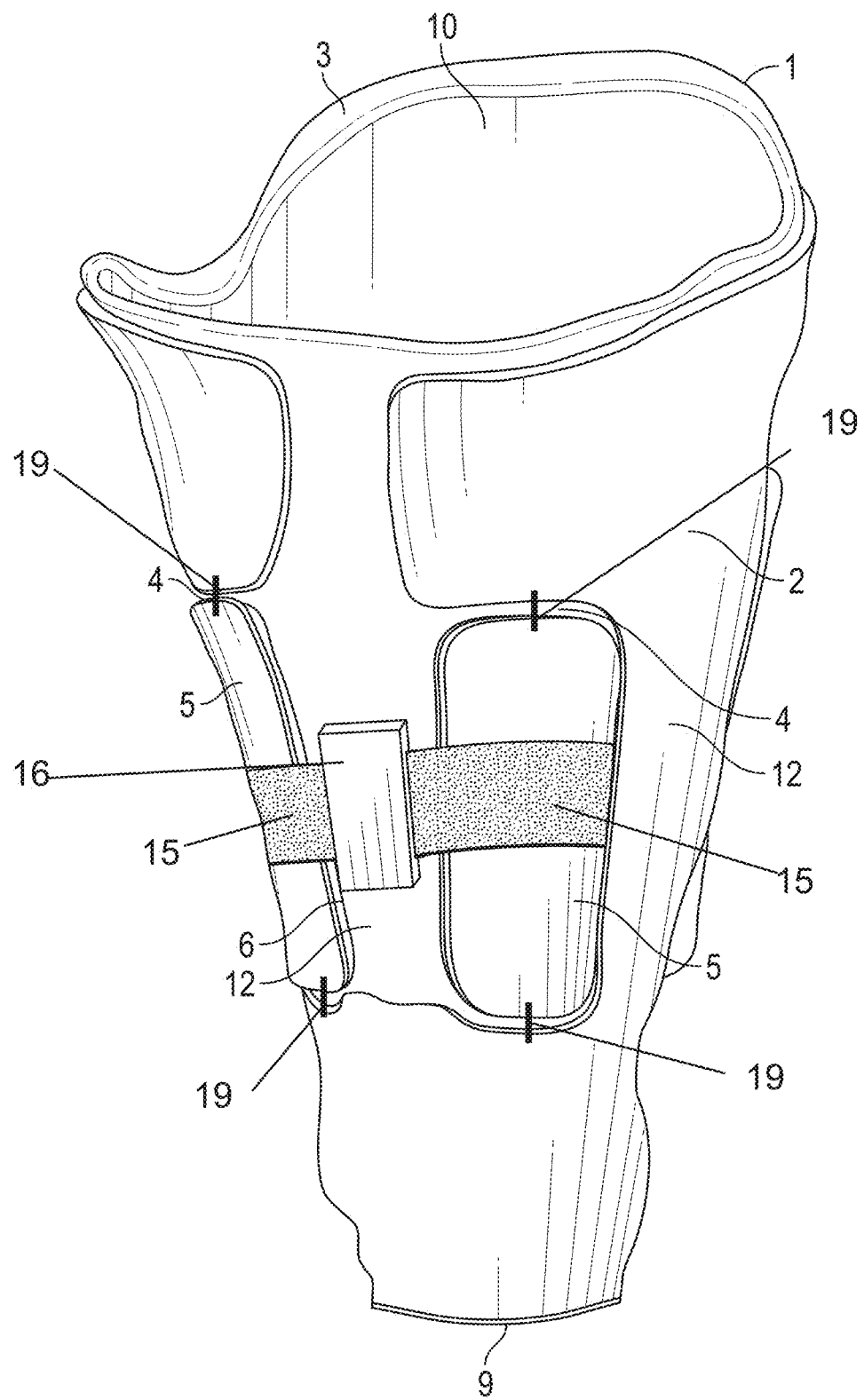
FIG. 8: is a front view of an interlaced disarticulated compression socket having a compression band coupled to a band coupler and securing a plurality of compression inserts in one embodiment thereof.
Figure 9:
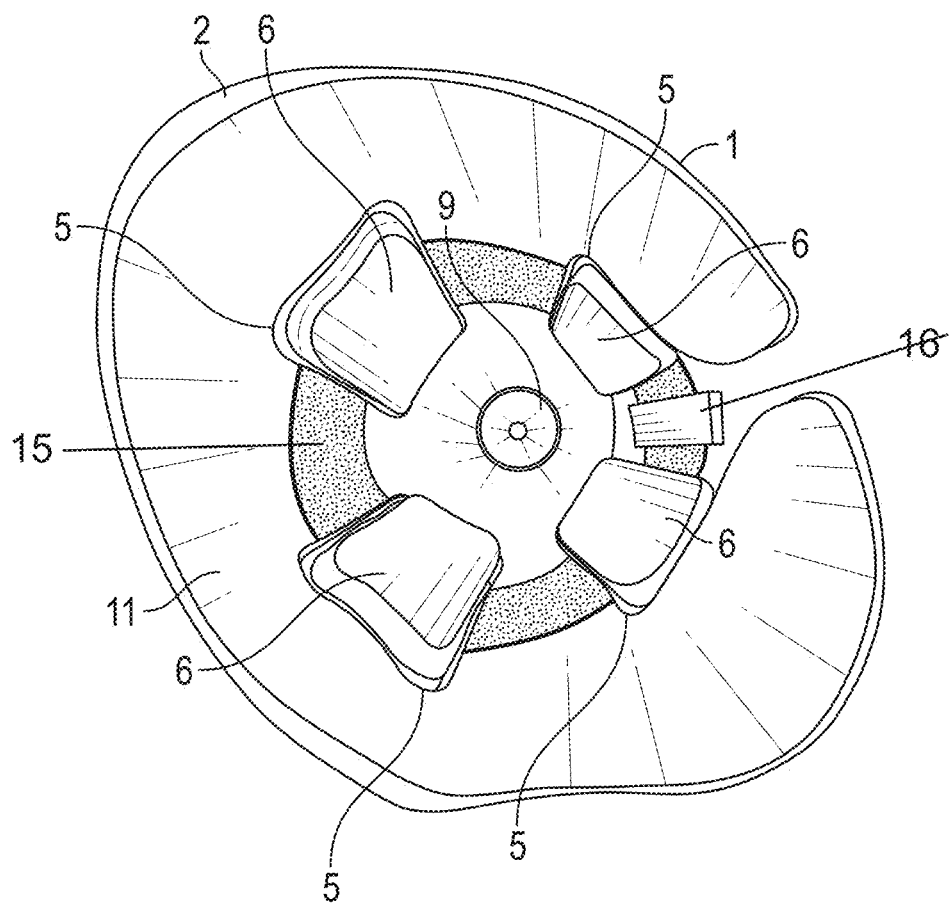
FIG. 9: is a top view of an interlaced disarticulated compression socket having a compression band coupled to a band coupler and securing a plurality of compression inserts in one embodiment thereof.

In addition, the inventive technology may accommodate a residual limb within a disarticulated compression socket (1). In a preferred embodiment expansion, lateral or otherwise may result in the increase of the volume of the residual limb interface (10) as shown in FIG. 3. As part of the invention, expansion, including lateral expansion of the coupled disarticulated compression inserts (5) may include, but not me limited to: expansion of the coupled disarticulated compression inserts (5) resulting in at least a 5% increase in the volume of the residual limb interface (10); expansion of the coupled disarticulated compression inserts (5) resulting in at least a 10% increase in the volume of the residual limb interface (10); expansion of the coupled disarticulated compression inserts (5) resulting in at least a 15% increase in the volume of the residual limb interface (10); expansion of the coupled disarticulated compression inserts (5) resulting in at least a 20% increase in the volume of the residual limb interface (10); expansion of the coupled disarticulated compression inserts (5) resulting in at least a 25% increase in the volume of the residual limb interface (10); and expansion of the coupled disarticulated compression inserts (5) resulting in at least a 30% increase in the volume of the residual limb interface (10). In one embodiment, the invention may include a disarticulated compression socket (1) having an interlaced compression system. As generally shown in FIGS. 7-9, in one preferred embodiment, a disarticulated compression socket (1) may include a plurality of compression apertures (4) that may further accommodate at least one disarticulated compression insert (5). In this embodiment, one or more compression bands (15) may be placed in an interlaced configuration to secure said disarticulated compression inserts (5) compression apertures (4). In this interlaced configuration, a compression band (15) may be positioned along the outer or external surface of the disarticulated compression inserts (5) and along the internal surface of the disarticulated compression socket (1). In this configuration, when a compression band (15) is constricted, the compression band may generate a lateral compressive force by the disarticulated compression inserts (5). This compressive force is restricted to the disarticulated compression inserts (5) and independent of the socket frame (2), such that the disarticulated compression inserts (5) may conform to the laterally positioned muscle groups of a residual limb allowing for a more efficient compression and securement of the residual limb in the prosthetic. In one preferred embodiment, a disarticulated compression inserts (5) may include an extended compression surface (6) between ¼ and 4 inches in thickness. In this embodiment, one or more compression bands (15) may extend horizontally across the disarticulated compression insert (5) in an interlaced configuration such that the extended compression surface (6) is positioned against the residual limb, and further extending beyond the surface of the socket frame (2). In this specific embodiment, one or more compression bands (15) are constricted the extended compression surface (6) may cause the disarticulated compression insert (5), which as noted above extends past the surface of the socket frame (2), to retract which may allow the disarticulated compression insert (5) to compresses in a manner similar to the lateral compression described herein as the retracting band is not retracting against the rigid frame of the socket frame (2), but the tractable surface of the extended compression surface (6).

While one or a plurality of compression bands (15) may be initially demonstrated as a band-like structure, such embodiments exemplary only as a variety of tightening or constricting components may be encompassed within the invention. For example, in one embodiment, a compression band (15) may include an elastic or even non-elastic strap that may be constricted to compress and secure a plurality of the disarticulated compression inserts (5) against a residual limb. Additional embodiments may include compression band (15) made from wire, cords, or cables among other materials.

In another preferred embodiment, one or more compression bands (15) may be adjustable. Again, referring to FIGS. 7-9, in one preferred embodiment, a compression band coupler (16) may secure and/or adjust one or more compression bands (15). In one embodiment, a compression band coupler (16) may be a mechanical component that may secure a compression band (15) in a desired position. In this preferred embodiments, a compression band coupler (16) include a buckle, strap lock, actuator, catch and/or adjuster that may allow a user to tighten (or loosen) the compression band (15) to a desired position and secure the band in that position to maintain a consistent level of force applied to the disarticulated compression inserts (5). Additional embodiments may include Velcro® coupler that may allow a compression band (15) to be tightened or loosened according to a user's desire.

In another embodiment, a compression band coupler (16) may include a compression aperture (4) that may be engaged to tightened or loosen a compression band (15), and preferably a wire or cord compression band (15). In this embodiment, a wire or cord compression band (15) may be placed externally over a disarticulated compression insert (5) or may be positioned internally within the disarticulated compression insert (5), for example in a cord channel (not shown).

In additional embodiments, where the compression band (15) may be positioned along the external surface of a disarticulated compression insert (5), it may be secured within a guide channel (17). In this embodiment, a guide channel may include a shaped depression or channel that may help position the compression band (15) and prevent it from moving out of a desired position. In still further embodiments, a band connector (18) may be formed to couple a compression band (15) with a disarticulated compression insert (5). In this embodiment, such a connector may be similar to a belt, such that holes along the compression band (15) may be slotted with extensions on the external surface of a disarticulated compression insert (5). Such an embodiment may preferably be employed when using an elastic or non-elastic compression band (15).

In still further embodiment, the disarticulated compression inserts (5) may be secured to a socket frame (2) through one or more insert adaptors (19). In this embodiment, one or more disarticulated compression insert (5) may be secured in a tractable connection with the socket frame (2) such that when a compression band (15) is loosened or remove such that user's residual limb may be removed from the disarticulated compression socket (1), the disarticulated compression inserts (5) may remain coupled to the socket frame (2), and further properly orientated within the compression aperture (4). This feature may make it easier to remove and/or adjust one or more a compression bands (15) without having to individually position a disarticulated compression socket (1).

Figure 10:
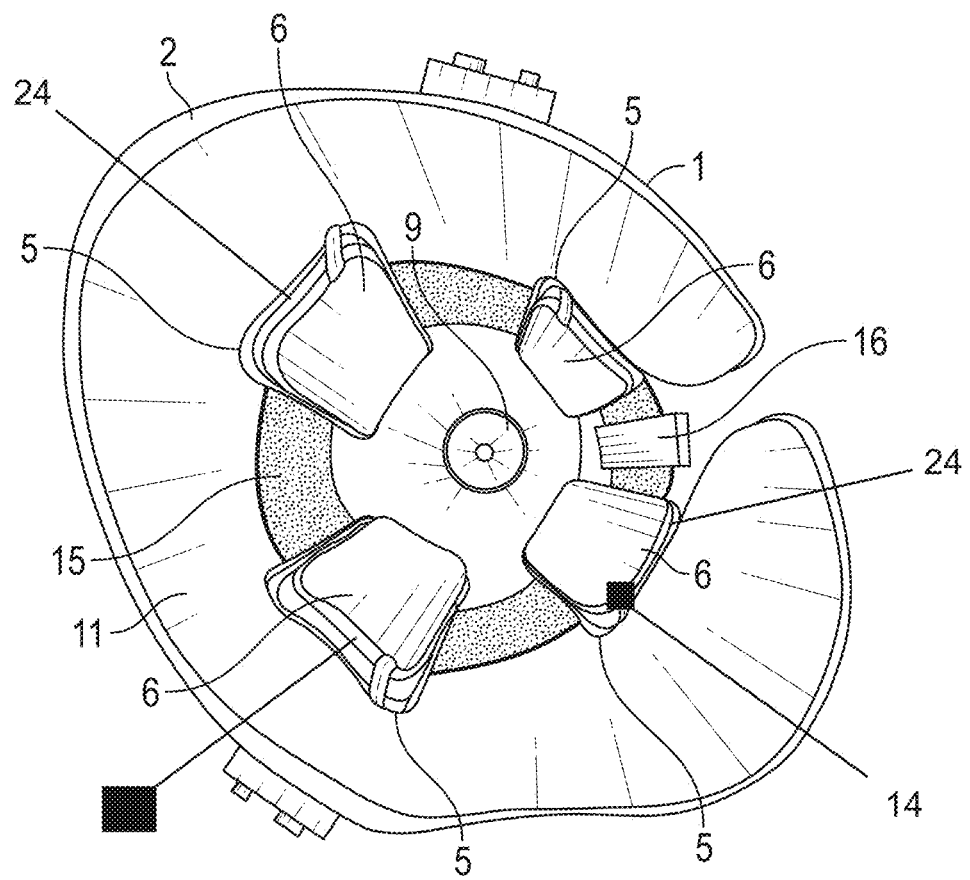
FIG. 10: is a top view of a disarticulated compression socket having an inflatable bladder integrated with a plurality of compression inserts in one embodiment thereof.
Figure 11:
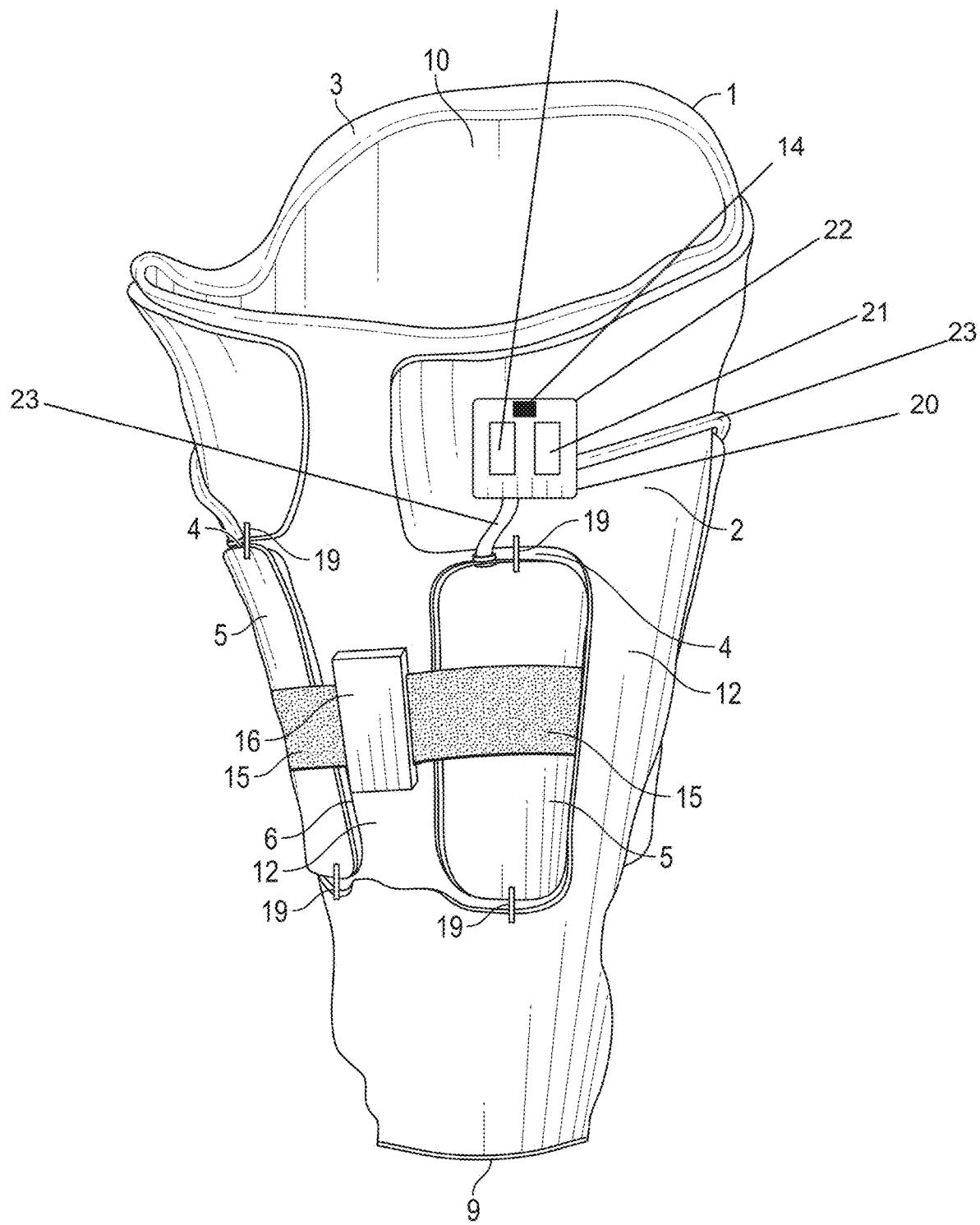
FIG. 11: is a front view of a disarticulated compression socket having an inflatable bladder integrated with a plurality of compression inserts in one embodiment thereof.

Referring now to FIGS. 10 and 11, in one preferred embodiment the inventive technology may include a disarticulated compression socket (1) having an inflatable system that may provide a customizable system to secure a residual limp within the socket frame (2). In this embodiment, on or more air pumps (21) may be coupled to socket frame (2). Such an air pump (21) may include a manual air pump, as well as an automatic air pump that may further include a power source. As shown again in FIGS. 10 and 11, an air pump (21) of the invention may include an inflation actuator (21) or a deflation actuator (22). In this configuration, an inflation actuator (21) may be a manual or a mechanical component that may act as an air valve to allow air from the external environment to be injected into one or more inflatable bladders (24) that may further be individual positioned on or within a disarticulated compression insert (5). In this configuration, a deflation actuator (22) may be a manual or a mechanical component that may act as a release valve and allow air from the external environment to be released from one or more inflatable bladders (24) individual positioned on or within a disarticulated compression inserts (5). As further shown in FIGS. 10 and 11, in one preferred embodiment, one or more air pumps (21) may be maintained in fluid communication with one or more inflatable bladders (24) through a tube (23).

Naturally, the above described embodiment is exemplary only. For example, in alternative embodiment, an air pump (21) may be detachable from the socket frame (2) or may be a stand-alone component that may be manually coupled and decoupled with an inflatable bladder (24). In still alternative embodiment, an inflation actuator (21) and/or deflation actuator (22) may include manually or automatically adjustable valves be positioned on an inflatable bladders (24) to permit air to into and out of the inflatable bladder depending on a user's desired level of inflation. As can be further understood, in one embodiment a plurality of inflatable bladders (24) may be individual positioned on or within a disarticulated compression insert (5) and may further be in fluid communication one with another such that they are responsive to a single pump (20) as well as inflation actuator (21) and/or deflation actuator (22). In this embodiment, the actions of the pump (20) as well as inflation actuator (21) and/or deflation actuator (22) may act in unison to inflate and deflate the a plurality of inflatable bladders (24) may be individual positioned on or within a disarticulated compression insert (5) providing an adjustable fitting mechanism for a user to control the pressure applied to secure a residual limb within the socket frame (2).

In another embodiment, a plurality of inflatable bladders (24) may be individual positioned on or within a disarticulated compression insert (5) and may be responsive to an individual pump (20) as well as inflation actuator (21) and/or deflation actuator (22). In this embodiment, each of said plurality of inflatable bladders (24) may be independently adjustable through the action of a corresponding pump=(20) as well as inflation actuator (21) and/or deflation actuator (22) providing a more fully-customizable adjustable fitting mechanism for a user to control the pressure applied to secure a residual limb within the socket frame (2).

As shown in FIG. 11, in one embodiment the invention may include a pump (20) that may be responsive to a signal, such as a wireless internet or cellular signal. In this embodiment, a software application may be established on a user's phone or other personal computing device that may be responsive to one or more sensors (26) that may detect the inflation level of an inflatable bladder or a compartment within an inflatable bladder (24). This application may send a signal to the pump (20) to adjust the amount of air in one or more inflatable bladders (24), for example through the engagement of an inflation actuator (21) and/or deflation actuator (22). In this embodiment, the application may adjust the amount of pressure exerted a residual limb positioned within the socket frame (2) by the one or more inflatable bladders (24), which may be automatically adjusted according to a pre-set threshold level, or may be individually adjusted from time-to-time by a user, again preferably through the application in this embodiment.

In another embodiment, the invention may include a vacuum adjustable disarticulated compression socket (1). Generally referring to FIGS. 12 and 13, in one preferred embodiment, a vacuum pump (25) may be positioned in fluid communication with one or more pressure attachment surface (27) through a tube (23). A pressure attachment surface (27) may include a surface having an extended suction surface feature that may be configured to generate a seal when adjacent to an external surface. In one preferred embodiment, a pressure attachment surface (27) may include one or more suction cup or other similar features that may be responsive to vacuum pump (25) and configured to form a seal with an external surface.

Figure 12:
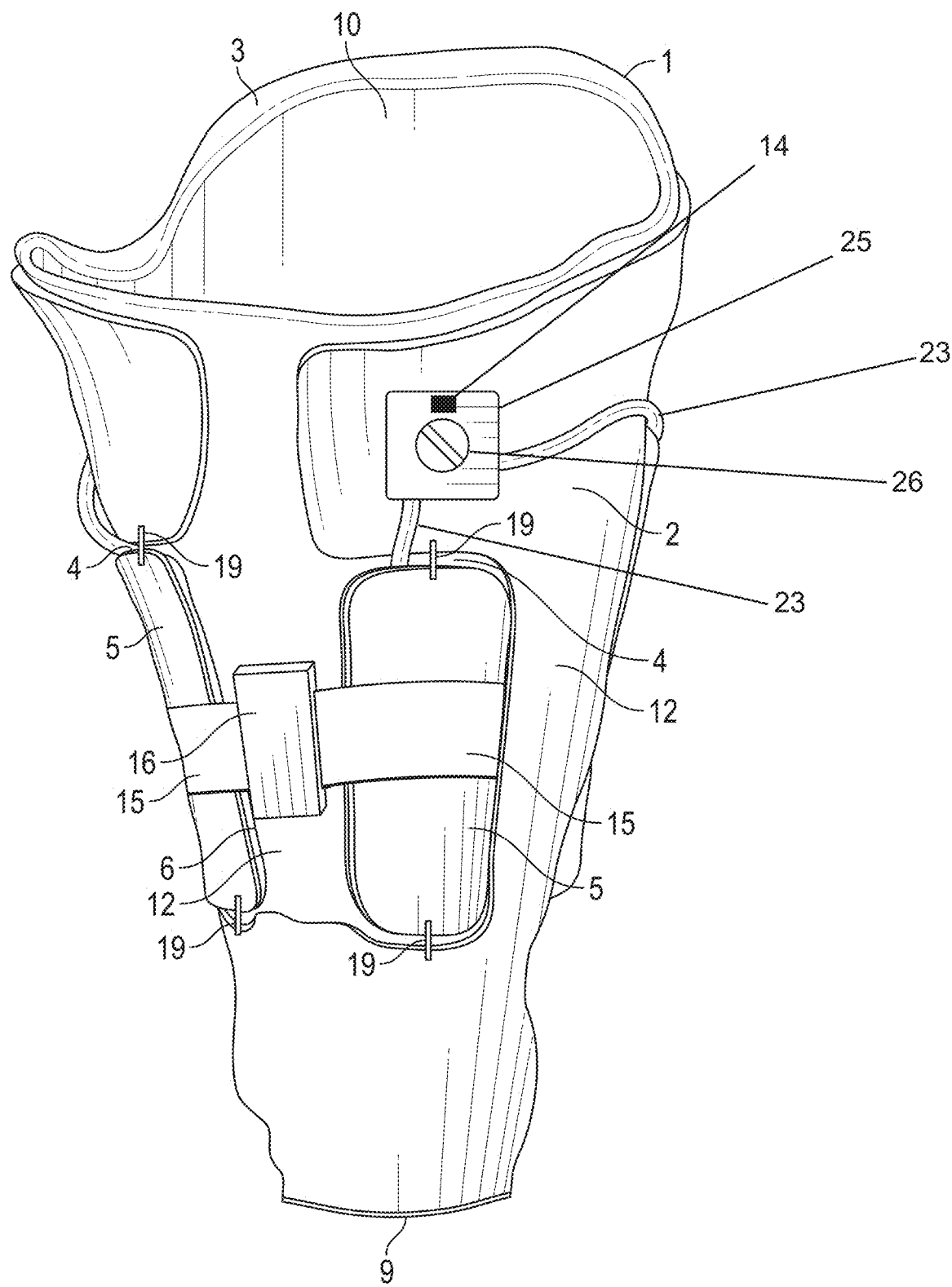
FIG. 12: a front view of a disarticulated compression socket having a vacuum coupler surface integrated with a plurality of compression inserts in one embodiment thereof.
Figure 13:
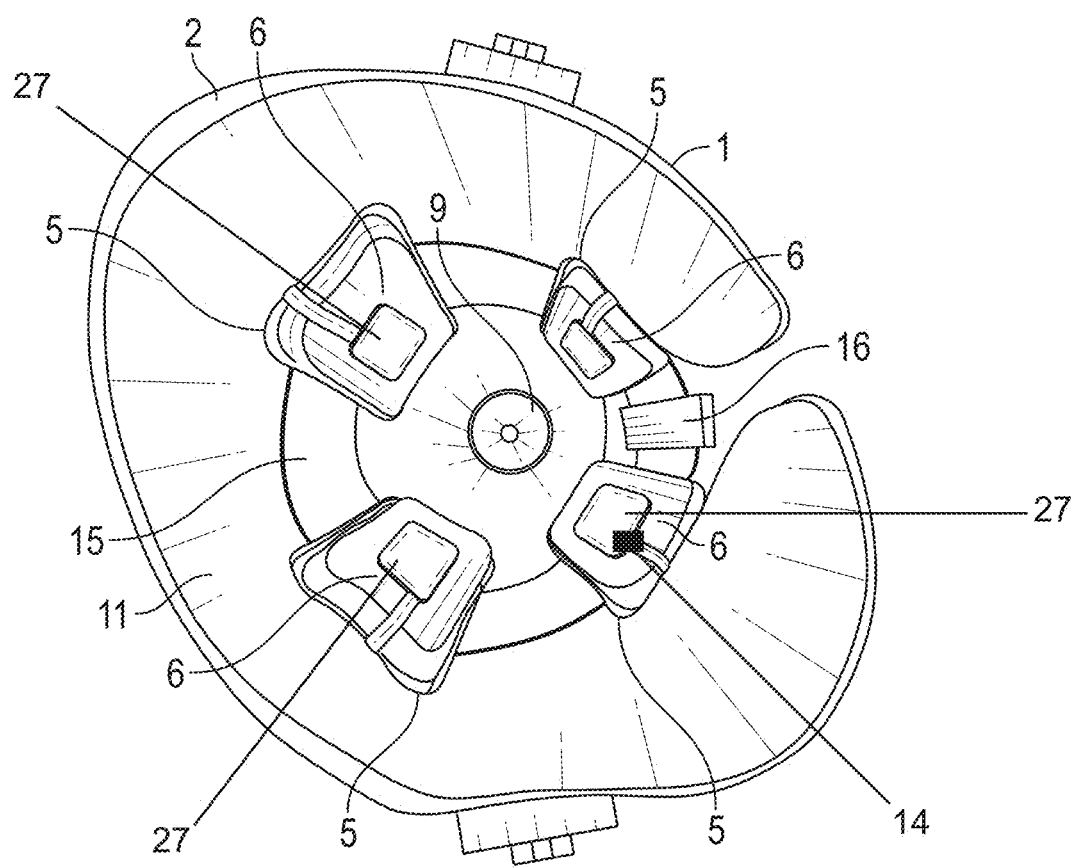
FIG. 13: is a top view of a disarticulated compression socket having a vacuum coupler surface integrated with a plurality of compression inserts in one embodiment thereof.

As shown in FIGS. 12 and 13, a residual limb may be positioned within a socket frame (2), and more preferably within an inner socket (2) configured to include a vacuum interface surface (28). In this preferred embodiment one or more pressure attachment surface (27) individual positioned on or within disarticulated compression inserts (5) may abut, or be coupled with a vacuum interface surface (28) on an inner socket—which may include, for example a generally tractable surface, preferably made of a silicon or other material that may allow it to be coupled with the pressure attachment surface (27) and form a seal. Again, in this preferred embodiment, a vacuum pump (25) may be activated through a vacuum actuator (26) which may draw air from the pressure attachment surface (27) generating a vacuum seal between a vacuum interface surface (28) on a user's residual limb, or more preferably a vacuum interface surface (28) of an inner socket (2). This vacuum seal may be adjustable to allow a customized level of attachment between the pressure attachment surface (27) and vacuum interface surface (28), Naturally, a vacuum actuator (26) may allow the vacuum seal to be release or decreased, for example through equalization of the pressure gradient between the outside air and the pressure seal. In one embodiment, a vacuum actuator (26) may include a release valve.

As noted above, in certain embodiments a vacuum pump (25) may be manually operated by a user to generate a customizable vacuum seal between the pressure attachment surface (27) and vacuum interface surface (28), while in additional embodiments such vacuum pump (25) may be operated automatically. In this embodiment, a software application may be established on a user's phone or other personal computing device that may be responsive to one or more sensors (26) that may detect the vacuum seal between the pressure attachment surface (27) and vacuum interface surface (28). This application may send a signal to the vacuum pump (25) to adjust the vacuum seal, for example through increasing the vacuum seal, for example through the engagement of a vacuum actuator (26). In this embodiment, the application may adjust the amount of pressure exerted a residual limb positioned within the socket frame (2) by the vacuum seal between the pressure attachment surface (27) and vacuum interface surface (28), which may be automatically adjusted according to a pre-set threshold level, or may be individually adjusted from time-to-time by a user, again preferably through the application in this embodiment.

As shown in FIGS. 14-17, in one embodiment the invention may include an improved 3-D printed disarticulated compression socket (30). In one preferred embodiment, a diagnostic evaluation of a patient in need of a prosthetic device may be performed and the initial three-dimensional shape of the residual limb may be digitally generated. The digital generation of this 3-D model may be captured by invasive, or non-invasive diagnostic techniques known in the art. In a preferred embodiment, this 3-D model of the residual limb may be digitally captured and communicated to a computer system that may further process the 3-D model and generate a digital output for a customized 3-D printed disarticulated compression socket (30) configured to conform to the shape of the 3-D model of the residual limb. In this embodiment, the digital output for a customized 3-D printed disarticulated compression socket (30) may be transmitted to a fabrication component or may be outputted into a CAD or other file format for automated mechanical or manual production. In another preferred embodiment, the computer system may upload the 3-D model and generate a digital output for a customized 3-D printed disarticulated compression socket (30) configured to conform to the shape of the 3-D model of the residual limb that may further be input into a 3-D fabrication device, such as a 3-D printer. The 3-D printing device may execute the 3-D model file and fabricate a rigid socket frame (2) and/or inner socket (3) configured to conform to the shape of the 3-D model of the residual limb. Generally, a rigid socket frame (2) and/or inner socket (3) generated by a rapid 3-D printing/prototyping process may be made from a variety of materials, and preferably composites, generally known in the art.

In one embodiment the invention may include disarticulated compression socket (1), and preferably a disarticulated 3-D printed compression socket (30) generated by a rapid 3-D printing/prototyping, further configured to have an improved replaceable compression system. As noted above, in certain embodiment, an anchor cord (8) may be positioned within and anchored to the body of the rigid socket frame (2) of a prosthetic. In the event the cord breaks, is damaged, or becomes unanchored from the rigid socket frame (2), replacement and correction of the anchor cord (8) may be extremely difficult and costly, and may, in some instances require the prosthetic device to be nearly completely broken or replaced.

Figure 19:
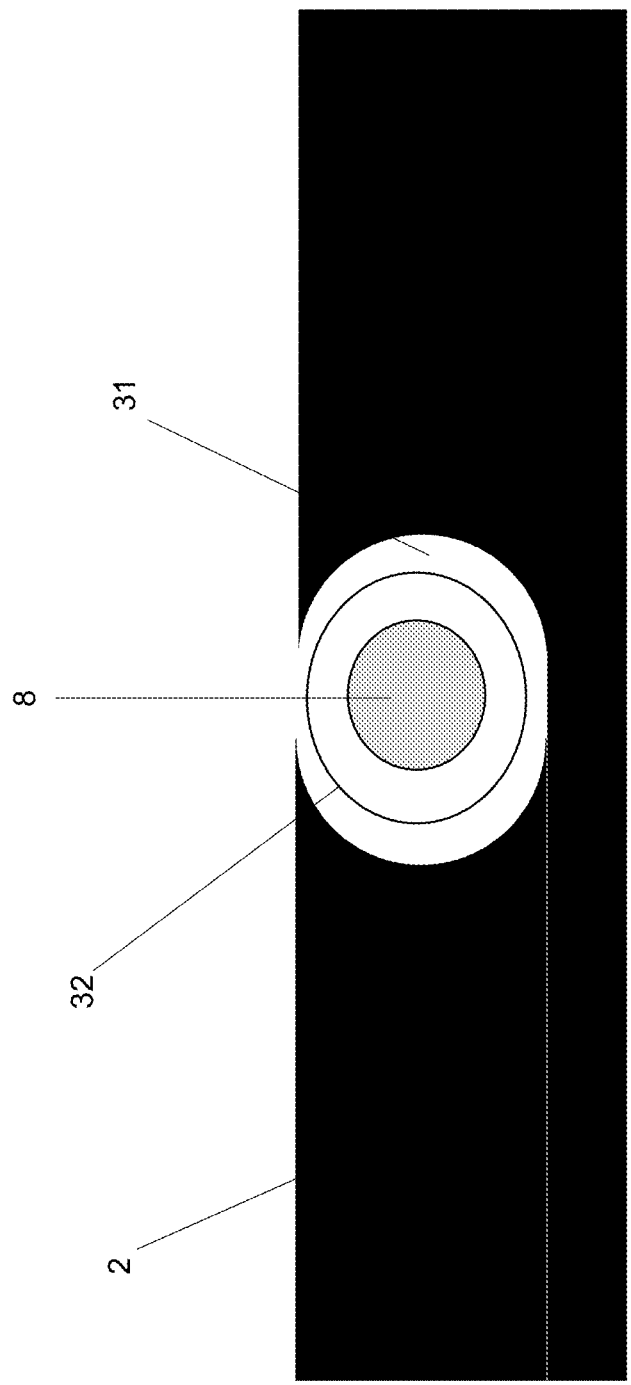
FIG. 19: shows a cross section of a 3-D printed disarticulated compression socket having a surface channel holding a removable cord cylinder on the internal surface of the rigid socket frame in one embodiment thereof.

To overcome the limitations described above, the invention may include disarticulated compression socket (1), and preferably a disarticulated 3-D printed compression socket (30) generated by a rapid 3-D printing/prototyping having an surface channel (31) positioned along the internal surface of the rigid socket frame (2). Generally referring now to FIGS. 14 and 19, in one preferred embodiment, a surface channel (31) may be configured to include an integral channel having an opening facing the internal surface of the rigid socket frame (2).

Figure 14:
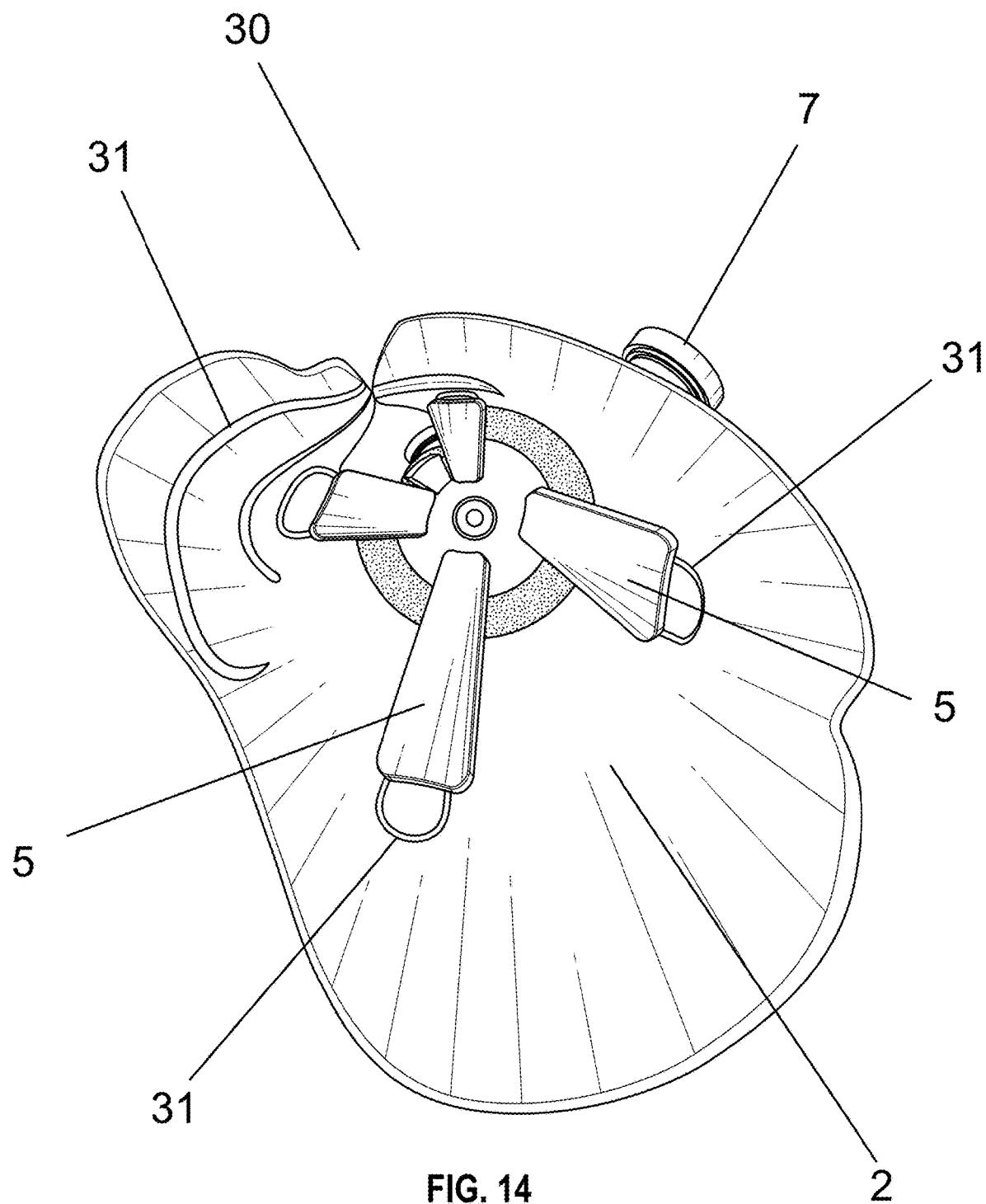
FIG. 14: is a top view of a 3-D printed disarticulated compression socket having an exposed surface channel positioned on the internal surface of the rigid socket frame holding a removable cord cylinder coupled with a plurality of disarticulated compression inserts in one embodiment thereof.
Figure 15:
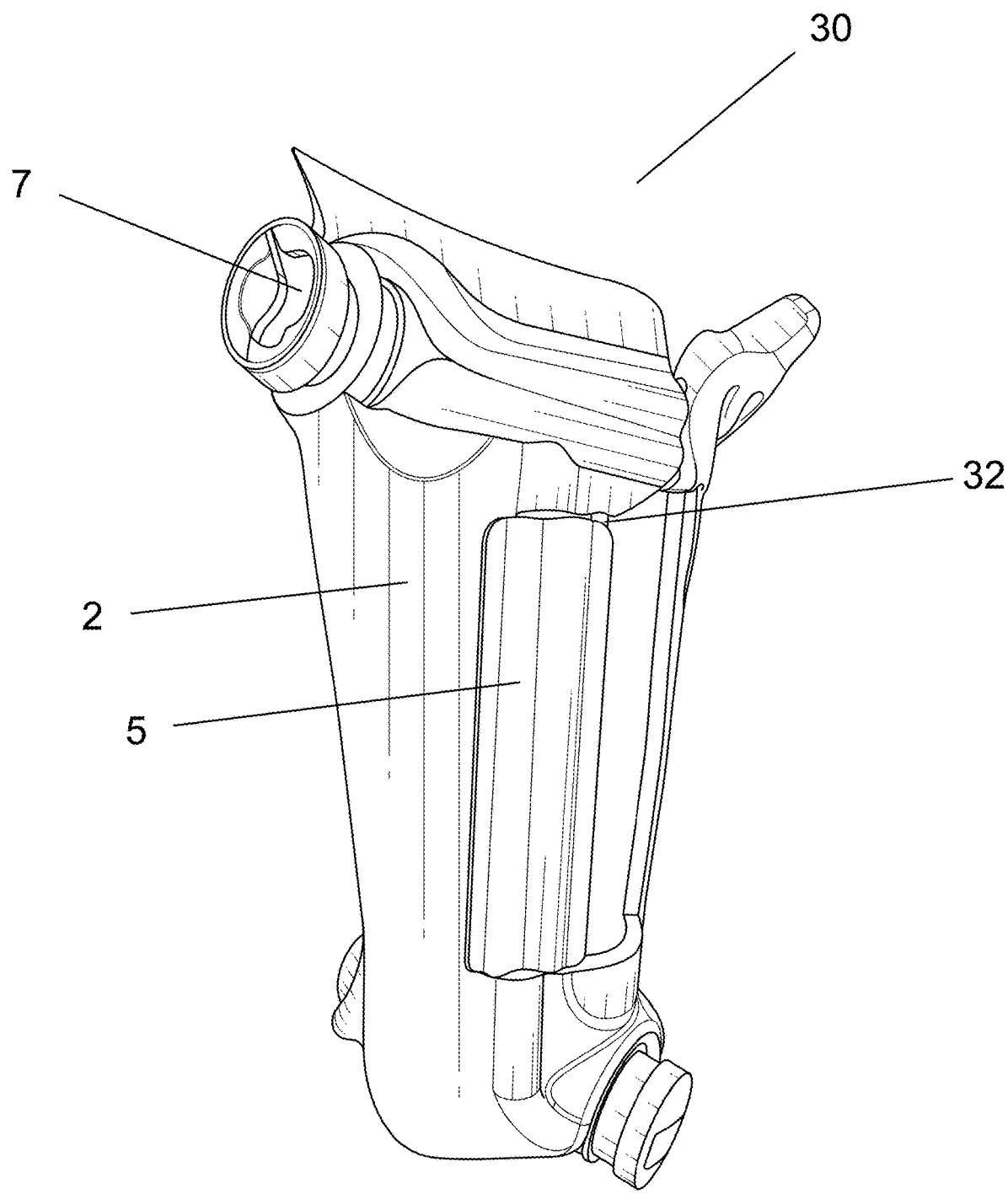
FIG. 15: is a side view of a 3-D printed disarticulated compression socket having a disarticulated compression inserts coupled with a removable cord cylinder positioned within a surface channel on the internal surface of the rigid socket frame in one embodiment thereof.
Figure 16:
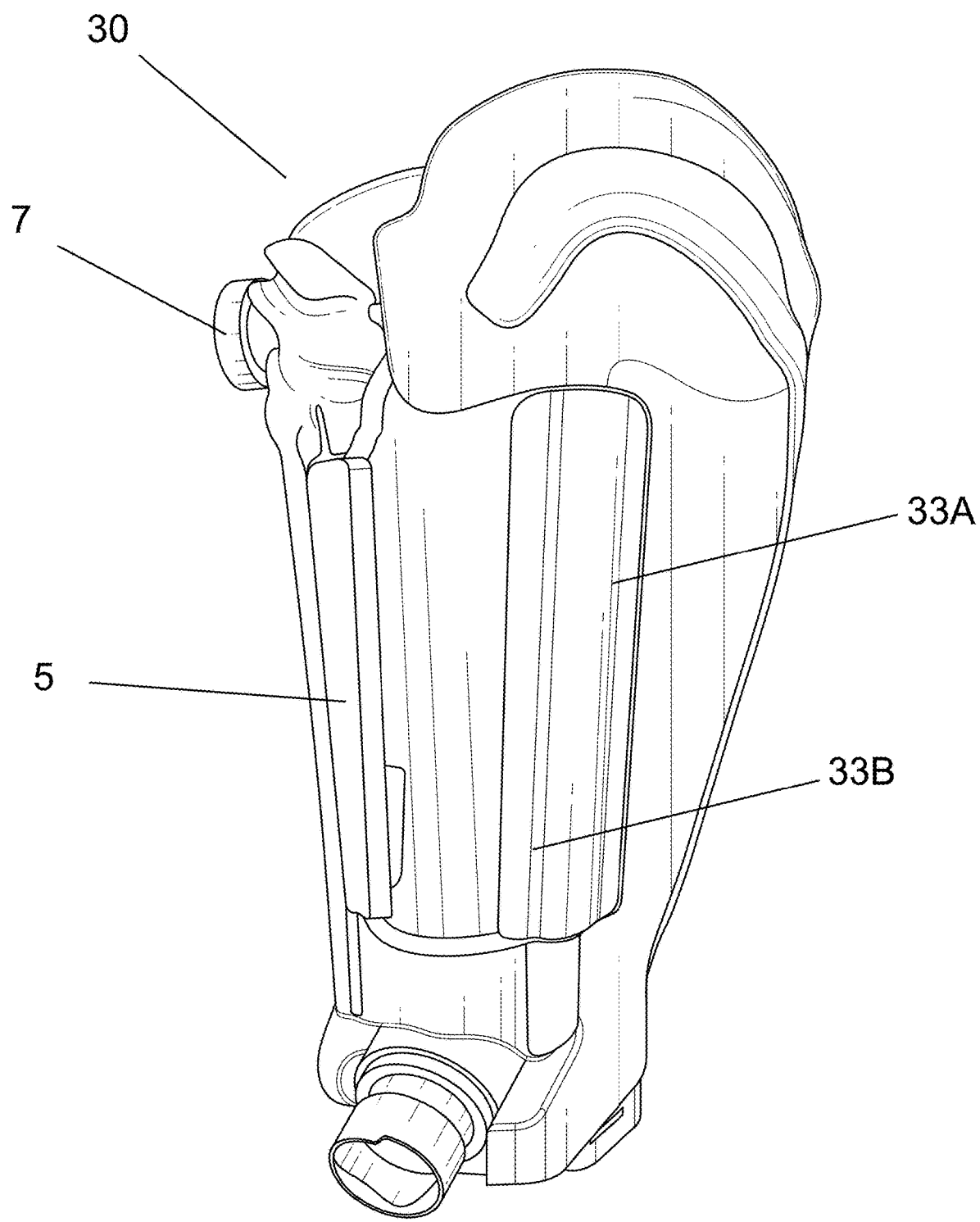
FIG. 16: is a side view of a 3-D printed disarticulated compression socket having a plurality of disarticulated compression inserts coupled with a removable cord cylinder positioned within a surface channel on the internal surface of the rigid socket frame in one embodiment thereof.
Figure 17:
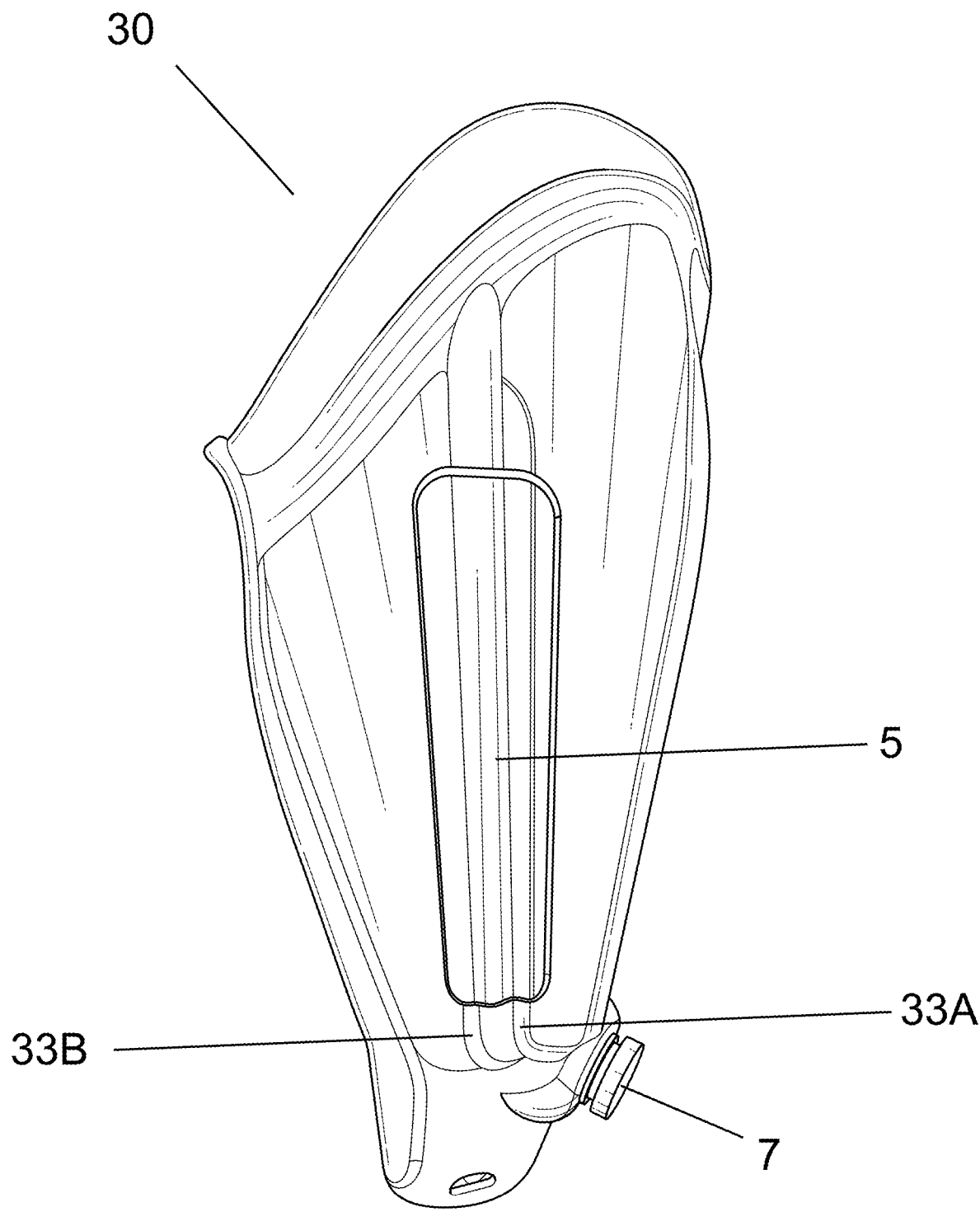
FIG. 17: is a rear view of a 3-D printed disarticulated compression socket having a disarticulated compression inserts coupled with a removable cord cylinder positioned within a surface channel on the internal surface of the rigid socket frame in one embodiment thereof.

As specifically shown in FIG. 14, the surface channel (31) of the invention may be configured to secure a removable cord cylinder (32). As further shown in FIG. 18-19, the cord cylinder (32) may be positioned around a compression cord (34) responsive to a compression actuator (7) such that activation of the compression actuator (7) causes the independent movement, or retraction of the compression cord (34) positioned within the cord cylinder (32). In this embodiment, the cord cylinder may be made of a material that facilitate the independent movement of the encased compression cord (34), such as Teflon®, thermoplastics or composite material.

In this embodiment, the compression cord (34) does not need to be anchored to the rigid frame (2) or device. Moreover, in the event compression cord (34) breaks, or loses tensile strength and requires replacement, a user can remove the cord cylinder (32) from the surface channel (31) of the rigid socket frame (2) and may either replace it with a new cord cylinder (32) and compression cord (34), or re-thread the cord cylinder (32) with a new compression cord (34). The new cord cylinder (32) and/or compression cord (34) may be re-secured within the surface channel (31) of the invention and further re-engaged with a compression actuator (7).

Figure 18:
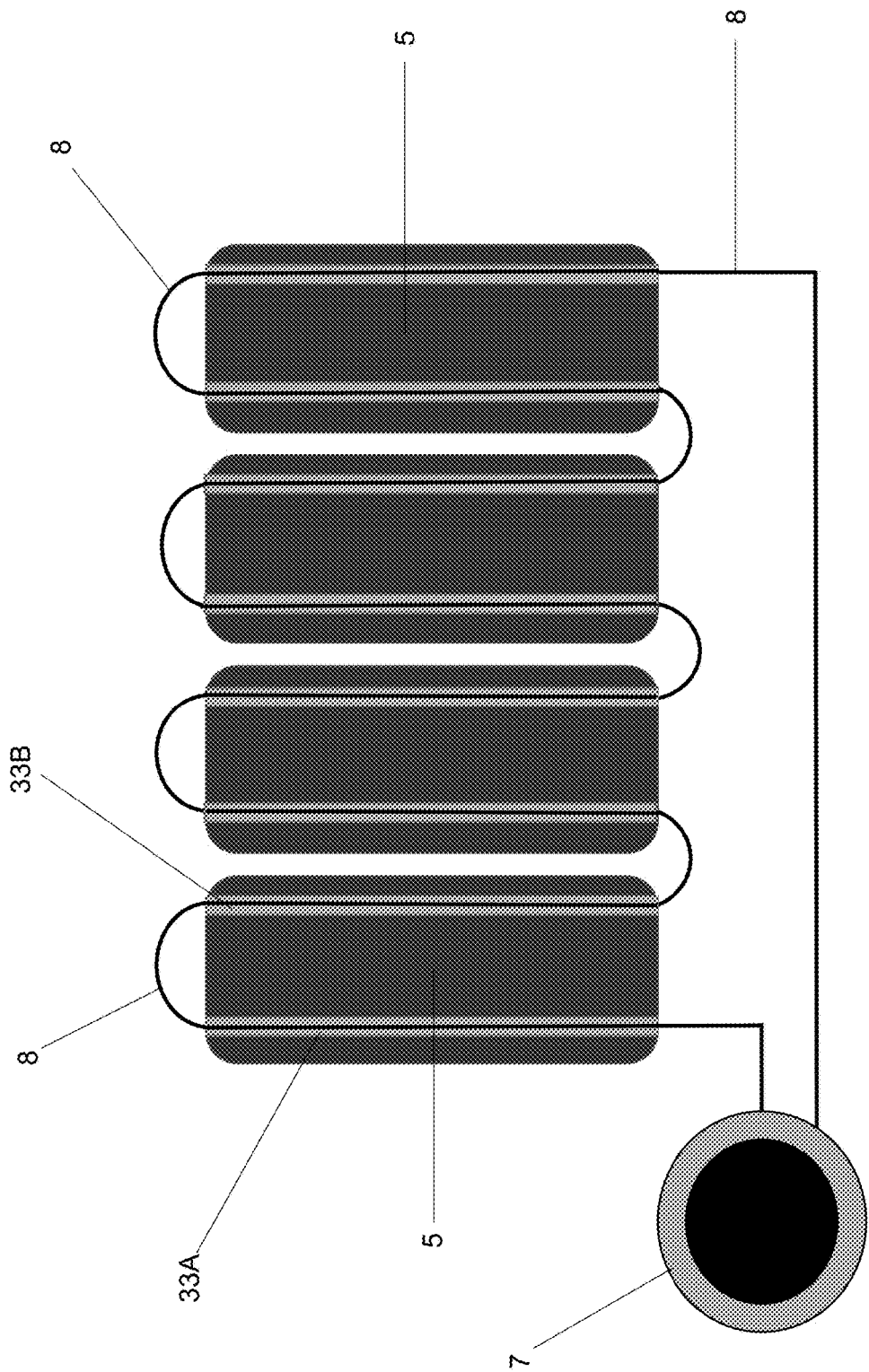
FIG. 18: shows a schematic diagram of a plurality of disarticulated compression inserts coupled with a removable cord cylinder holding an exemplary cord positioned within a surface channel on the internal surface of the insert that is further responsive to a compression actuator that when engaged retracts the cord and causes the disarticulated compression inserts to compress towards the user's residual limb in one embodiment thereof.

As shown specifically in FIGS. 14 and 18, in one preferred embodiment the disarticulated compression socket (1), and preferably a disarticulated 3-D printed compression socket (30) generated by a rapid 3-D printing/prototyping, may be configured with a surface channel (31) along the internal surface of the socket frame (2), wherein the surface channel is positioned along the frame where a user may want or require a compression force to be applied. Specifically referring to FIG. 18, in one preferred embodiment a disarticulated compression socket (1), and preferably a disarticulated 3-D printed compression socket (30) generated by a rapid 3-D printing/prototyping, may be configured having one or a plurality of disarticulated compression inserts (5) having one or more insert channels (33). In this preferred embodiment, an insert channel (33) may be configured to secure a removable cord cylinder (32) having an internally positioned compression cord (34) responsive to at least one cord actuator (7) such that activation of the cord actuator (7) may cause the compression cord (34) to retract causing the disarticulated compression insert (5) to compress against a residual limb positioned within the internal cavity of the socket frame (2).

As further shown in FIG. 18, in this embodiment a plurality of disarticulated compression inserts (5) may be responsive to a single compression actuator (7) through a compression cord (34). In this embodiment, a cord cylinder (32) securing a compression cord (34) responsive to a single compression actuator (7) may be further secured within an insert channel (33) along the internal surface of a rigid socket frame (2) of the invention. As further shown in FIG. 18, the cord cylinder (32) securing a compression cord (34) may cross-over from the surface channels (33) of the rigid socket frame (2) and be secured within a first insert channel (33), which in this embodiment pass along the length of a disarticulated compression insert (5). In this embodiment, the first insert channel (33) may be positioned internally within the disarticulated compression insert (5), while in alternative embodiments it may be positioned within an insert channel (33) positioned along the internal surface of the socket frame (2).

Again referring to FIG. 18, in this embodiment, the compression cord (34), positioned within a cord cylinder (32), may cross-over from the first insert channel (33) of the disarticulated compression insert (5) and be secured within a surface channel (33) positioned along the internal surface of the socket frame (2). Again, the compression cord (34), positioned within a cord cylinder (32), may cross-over from the surface channel (33) positioned along the internal surface of the socket frame (2) and be secured within a second insert channel (33) of the disarticulated compression insert (5). As further shown in FIG. 18, in this manner, a plurality of disarticulated compression inserts (5) may be coupled together by a compression cord (34), positioned within a cord cylinder (32), and be made responsive to, in this embodiment a single compression actuator (7), such that activation of the single compression actuator (7) may generate the synchronous retraction or compression of the coupled disarticulated compression inserts (5).

Notably, while in this embodiment the first and second insert channels (33) are positioned length wise along the disarticulated compression inserts (5), in alternative embodiments first and second insert channels (33) may be positioned horizontally and operate in a similar fashion as described above to generate a synchronous retraction or compression of the coupled disarticulated compression inserts (5). Also, in additional embodiment, a cord cylinder (32) may form a single unbroken component that is positioned within both the surface channels (33) insert channels (33) of the invention, while in alternative embodiment a cord cylinder (32) may be configured in a discontinuous manner such that it may be positioned within surface channels (33) insert channels (33), but not across the gap between the frame socket (2) and disarticulated compression inserts (5).

Figure 20A:
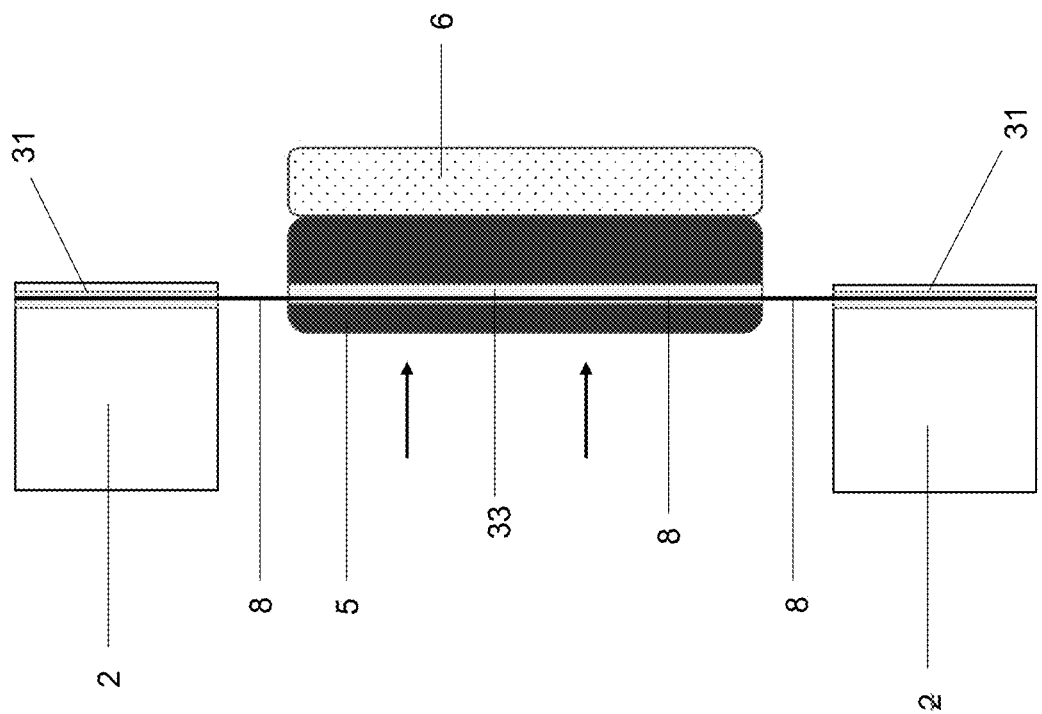
FIG. 20A: shows a diagram of an isolated of a disarticulated compression insert secured by a cord in an un-tensioned configuration cylinder positioned on the surface channel on the internal surface of the rigid socket frame in an off-set configuration.
Figure 20B:
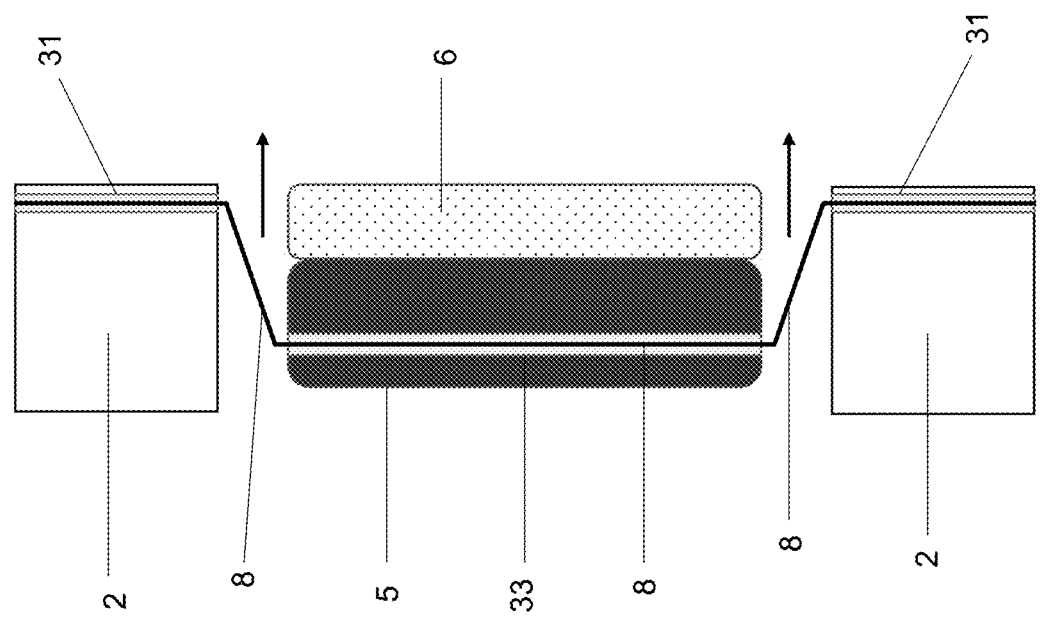
FIG. 20B: shows a diagram of an isolated of a disarticulated compression insert secured by a cord cylinder positioned on the surface channel on the internal surface of the rigid socket frame in an off-set configuration where the cord has been tensioned by a compression actuator causing the insert to compress towards the user's residual limb in one embodiment thereof.

The invention may include a disarticulated compression socket (1), and preferably a disarticulated 3-D printed compression socket (30) generated by a rapid 3-D printing/prototyping, configured to exhibit enhanced compression of the residual limp positioned within the frame socket (2). Generally referring to FIG. 20, a this preferred embodiment, a 3-D disarticulated compression socket (30) having a disarticulated compression insert (5) having one or more insert channels (33) that are positioned in an off-set or staggered configuration compared to a surface channel (31) on the internal surface of a rigid socket frame (2). In this preferred embodiment, activation of the cord actuator (7) may cause the compression cord (34) to retract causing the disarticulated compression insert (5) to compress against the residual limb positioned within the internal cavity of the socket frame (2), wherein the staggered configuration generates a longer transit distance of the disarticulated compression insert (5) generating enhanced compression against a residual limb positioned within the internal cavity of the socket frame (2), than if the surface channels (31) and insert channels (33) were approximately aligned.

In one embodiment, the extended compression surface (6) may be configured to have sufficient width that when the residual limb is positioned within the internal cavity of the socket frame (2) the disarticulated compression insert (5) is pushed outward forming the staggered alignment of the surface channels (31) and insert channels (33). In this embodiment the compression cord (34) may initially be configured to be sufficiently loose to allow the expansion of the disarticulated compression insert (5) in response to the insertion of the residual limb into the frame socket (2). As noted above, the compression actuator (7) may be adjusted by the user to increase or decrease compression as needed.

In additional embodiment, a compression cord (34) may be position directly within a surface channel and/or an insert channel, while it may optionally be positioned within a cord cylinder (32) that may be secured within a surface channel and/or an insert channel of the invention Naturally, all embodiments discussed herein are merely illustrative and should not be construed to limit the scope of the inventive technology consistent with the broader inventive principles disclosed. As may be easily understood from the foregoing, the basic concepts of the present inventive technology may be embodied in a variety of ways. It generally involves systems, methods, techniques as well as devices to accomplish a disarticulated compression socket and the like. In this application, the methods and apparatus for the aforementioned systems are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the statements of invention. As can be easily understood from the foregoing, the basic concepts of the present invention may be embodied in a variety of ways. It involves both techniques as well as devices to accomplish the appropriate system. In this application, the techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention may be described in some instances in method-oriented terminology, each element of the claims corresponds to a device and vice versa. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing the explicit embodiment(s) shown, the great variety of implicit alternative embodiments, and the broad methods or processes and the like are encompassed by this disclosure and may be relied upon when drafting any claims. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "support" should be understood to encompass disclosure of the act of "supporting"—whether explicitly discussed or not—and, conversely, were there effectively disclosure of the act of "supporting", such a disclosure should be understood to encompass disclosure of a "supporting method and/or technique, and/or device" and even a "means for supporting." Such changes and alternative terms are to be understood to be explicitly included in the description.

Any patents, publications, or other references mentioned in this application for patent, such as in the specification or an IDS are hereby incorporated herein by reference in their entirety. Any priority case(s) claimed by this application is hereby appended and hereby incorporated herein by reference in their entirety. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated herein by reference in their entirety. Finally, all references listed in the list of References To Be Incorporated By Reference In Accordance With The Patent Application or other information disclosure statement and the like filed with the application are hereby appended and hereby incorporated herein by reference in their entirety, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the methods and/or apparatus for providing a disarticulated compression socket as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in Hakim v. Cannon Avent Group, PLC, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. It should be understood that this application also provides support for any combination of elements in the claims and even incorporates any desired proper antecedent basis for certain claim combinations such as with combinations of method, apparatus, process, and the like claims.

Any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon. The inventive subject matter is to include, but certainly not be limited as, a system substantially as herein described with reference to any one or more of the Figures and Description (including the following: for example, the process according to any claims and further comprising any of the steps as shown in any Figures, separately, in any combination or permutation).

Finally, Applicant reserves the right to seek additional design patent protection over the claimed invention; such that the drawings are fully enabled so as to allow one of ordinary skill in the art to know that the claimed design was in Applicant's possession at the time of filing. As such, it should be noted that any broken lines are to be included for the purpose of illustrating environmental matter and form no part of the claimed design should such become necessary.

What is claimed is:

1. A disarticulated compression socket comprising:
a socket frame configured to secure a residual limb;
at least one inner socket configured to secure a residual limb through a residual limb interface;
a plurality of compression apertures on said socket frame;
a disarticulated compression insert positioned within each of said compression apertures;
a surface channel on said socket frame;
at least one insert channel on each of said disarticulated compression inserts positioned adjacent to at least one surface channel, wherein said surface channel and said insert channel are positioned lengthwise along said disarticulated compression insert;
a cord cylinder configured to be positioned within the surface channel and the insert channel;
a compression cord positioned within said cord cylinder and responsive to a compression actuator, wherein activation of said compression actuator causes the lengthwise retraction of said compression cord positioned within said cord cylinder further causing the coordinated lengthwise inward compression of each of said disarticulated compression inserts securing said residual limb within said socket frame;
wherein the coordinated lengthwise inward compression of each of said disarticulated compression inserts allows 5% or greater reduction in the volume of said residual limb interface.

2. The disarticulated compression socket of claim 1, wherein said socket frame comprises a 3-D printed socket frame.

3. The disarticulated compression socket of claim 1, wherein said a 3-D printed socket frame comprises a 3-D printed socket frame selected from the group consisting of: a transfemoral socket frame; a transhumeral socket frame; a transradial socket frame; a transtibial socket frame; a symes socket frame; a hip disarticulation socket frame; a knee disarticulation socket frame; and a wrist disarticulation socket frame.

4. The disarticulated compression socket of claim 1, wherein said inner socket comprises a 3-D printed inner socket.

5. The disarticulated compression socket of claim 1, and further comprising at least one extended compression surface coupled with each of said disarticulated compression inserts.

6. The disarticulated compression socket of claim 5, wherein said extended compression surface comprises an extended compression surface selected from the group consisting of: a compressive extended compression surface; a plastic extended compression surface; a gel extended compression surface; a silicone extended compression surface; an air filled extended compression surface; a foam extended compression surface; and a composite extended compression surface.

7. The disarticulated compression socket of claim 1, wherein said compression actuator comprises a compression actuator selected from the group consisting of: a strap compression actuator; an air pressure compression actuator; an automatic compression actuator; a twist compression actuator; and a detachable compression actuator.

8. The disarticulated compression socket of claim 1, and further comprising a plurality of release channels configured to accommodate soft tissue expansion of said residual limb when said disarticulated compression inserts are compressed to secure said residual limb within said socket frame.

9. The disarticulated compression socket of claim 1, wherein said compression socket is configured to allow a 8.5% reduction in the volume of the residual limb interface.

10. The disarticulated compression socket of claim 1, wherein said compression socket is configured to allow a greater than 10% reduction in the volume of the residual limb interface.

11. The disarticulated compression socket of claim 1, wherein said cord cylinder comprises a single continuous cord cylinder positioned within the surface channel and the insert channel.

12. The disarticulated compression socket of claim 1, wherein said disarticulated compression inserts comprise a plurality of opposing disarticulated compression inserts.

13. The disarticulated compression socket of claim 1, wherein said surface channel on the socket frame and the insert channel on the disarticulated compression inserts are configured in a staggered position.

14. The disarticulated compression socket of claim 13, wherein said surface channel on the socket frame and the insert channel on the disarticulated compression inserts configured in a staggered position such that the compression cord responsive to said compression actuator extends lengthwise through each of said disarticulated compression inserts.

15. A compression prosthetic comprising:
a socket frame configured to secure a residual limb;
at least one inner socket configured to secure a residual limb through a residual limb interface;
a plurality of compression apertures on said socket frame;
a disarticulated compression insert positioned within each of said compression apertures;
at least one surface channel positioned approximate to the inner surface of said socket frame;
at least one insert channel positioned approximate to the external surface on each of said disarticulated compression inserts positioned adjacent to at least one surface channel, wherein said surface channel and said insert channel are aligned lengthwise along said disarticulated compression insert;
a cord cylinder configured to be positioned within the surface channel and the insert channel;
a compression cord positioned within said cord cylinder and responsive to a compression actuator, wherein activation of said compression actuator causes the lengthwise retraction of said compression cord further causing the coordinated lengthwise inward compression of each of said disarticulated compression inserts securing said residual limb within said socket frame; and
wherein the surface channel on said socket frame and the insert channel on said disarticulated compression inserts are configured in a staggered position such that when said actuator is not activated, said compression insert is positioned approximate to said residual limb while the surface channel and the insert channel are not aligned, and wherein activation of said compression actuator causes the lengthwise retraction of said compression cord towards the residual limb for said disarticulated compression insert in response to said compression actuator until the surface channel and the insert channel are approximately aligned along the inner surface of said frame socket;
wherein the coordinated lengthwise inward compression of each of said disarticulated compression inserts allows 5% or greater reduction in the volume of said residual limb interface.

16. The compression prosthetic of claim 15, wherein said surface channel on the socket frame and the insert channel on the disarticulated compression inserts configured in a staggered position such that the compression cord responsive to said compression actuator extends lengthwise through each of said disarticulated compression inserts.

17. The compression prosthetic of claim 15, wherein said compression socket is configured to allow an 8.5% reduction in the volume of the residual limb interface.

18. The compression prosthetic of claim 15, wherein said compression socket is configured to allow a greater than 10% reduction in the volume of the residual limb interface.

\* \* \* \* \*